United States Patent [19]
Andrási et al.

[11] Patent Number: 5,536,832
[45] Date of Patent: Jul. 16, 1996

[54] N-ACYL-2,3-BENZODIAZEPINE DERIVATIVES PHARMACEUTICAL COMPOSITIONS CONTAINING THEM AND PROCESS FOR PREPARING SAME

[75] Inventors: Ferenc Andrási; Pál Berzsenyi; Péter Botka; Sándor Farkas; Katalin Goldschmidt; Tamás Hámori; Jenó Kórösi; Imre Moravcsik; István Tarnawa, all of Budapest, Hungary

[73] Assignee: Gyogyszerkutato Intezet KFT, Budapest, Hungary

[21] Appl. No.: 423,153

[22] Filed: Apr. 17, 1995

Related U.S. Application Data

[60] Division of Ser. No. 80,604, Jun. 21, 1993, Pat. No. 5,459, 137, which is a continuation-in-part of Ser. No. 48,347, Apr. 15, 1993, abandoned, which is a continuation-in-part of Ser. No. 809,361, Dec. 17, 1991, abandoned.

[30] Foreign Application Priority Data

Dec. 21, 1990 [HU] Hungary .................. 83 98/90

[51] Int. Cl.⁶ .................... A61K 31/55; C07D 491/056
[52] U.S. Cl. ........................... 540/557; 514/221
[58] Field of Search ........................... 540/557

[56] References Cited

FOREIGN PATENT DOCUMENTS 2194236  3/1988  United Kingdom .................. 540/557

*Primary Examiner*—Robert T. Bond
*Attorney, Agent, or Firm*—Keil & Weinkauf

[57] ABSTRACT

The invention relates to novel N-acyl-2,3-benzodiezapine derivatives of the general formula (I), their stereoisomers and acid-addition salts, pharmaceutical compositions containing them and a process for their preparation. In the general formula (I)

R stands for a $C_{1-6}$ alkanoyl group optionally substituted by a methoxy, cyano, carboxyl, amino, $C_{1-4}$ alkylamino, di($C_{1-4}$ alkyl)amino, pyrrolidino, phthalimido or phenyl group, or by one or more halogen(s); or R is a benzoyl, cyclopropanecarbonyl, $C_{1-5}$ alkylcarbamoyl or phenylcarbamoyl group; or R is absent when a double bond exists between the N(3) and C(4) atoms;

$R^1$ means hydrogen; or $R^1$ is absent when a double bond exists between the N(3) and C(4) atoms;

$R^2$ means a $C_{1-3}$ alkyl group; or $R^1$ and $R^2$ together stand for a methylene group and no double bond is present between the N(3) and C(4) atoms;

$R^3$ means hydrogen or a $C_{1-4}$ alkanoyl group;

$R^4$ represents hydrogen; a $C_{1-6}$ alkanoyl group optionally substituted by a methoxy, cyano, carboxyl, amino, $C_{1-4}$ alkylamino, di($C_{1-4}$ alkyl)amino, pyrrolidino, phthalimido or phenyl group or by one or more halogen(s); as well as a benzoyl, palmitoyl, cyclopropane-carbonyl, $C_{1-5}$ alkylcarbamoyl or phenylcarbamoyl group; and the dotted lines represent valence bonds optionally being present, with the proviso that no double bond exists between the N(3) and C(4) atoms when both $R^3$ and $R^4$ stand for hydrogen.

The compounds of the general formula (I) possess valuable central nervous system effects, particularly muscle-relaxant, anticonvulsive and neuroprotective action. Thus, they may be useful for the treatment of various diseases of central nervous system origin.

6 Claims, No Drawings

N-ACYL-2,3-BENZODIAZEPINE DERIVATIVES PHARMACEUTICAL COMPOSITIONS CONTAINING THEM AND PROCESS FOR PREPARING SAME

This application is a divisional application of U.S. application Ser. No. 08/080,604, filed Jun. 21, 1993, now U.S. Pat. No. 5,489,137, which is a continuation-in-part of now abandoned U.S. application Ser. No. 08/048,347, filed Apr. 15, 1993, which is a continuation-in-part of now abandoned U.S. application Ser. No. 07/809,361, filed Dec. 17, 1991.

This invention relates to novel N-acyl-2,3-benzodiazepine derivatives of the general formula (I)

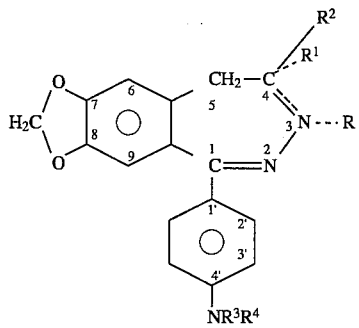

wherein

R stands for a $C_{1-6}$ alkanoyl group optionally substituted by a methoxy, cyano, carboxyl, amino, $C_{1-4}$ alkylamino, di($C_{1-4}$ alkyl)amino, pyrrolidino, phthalimido or phenyl group, or by one or more halogen(s); or R is a benzoyl, cyclopropanecarbonyl, $C_{1-5}$ alkylcarbamoyl or phenylcarbamoyl group; or R is absent when a double bond exists between the N(3) and C(4) atoms;

$R^1$ means hydrogen; or $R^1$ is absent when a double bond exists between the N(3) and C(4) atoms;

$R^2$ means a $C_{1-3}$ alkyl group; or $R^1$ and $R^2$ together stand for a methylene group and no double bond is present between the N(3) and C(4) atoms;

$R^3$ means hydrogen or a $C_{1-4}$ alkanoyl group;

$R^4$ represents hydrogen; a $C_{1-6}$ alkanoyl group optionally substituted by a methoxy, cyano, carboxyl, amino, $C_{1-4}$ alkylamino, di($C_{1-4}$ alkyl)amino, pyrrolidino, phthalimido or phenyl group or by one or more halogen(s); as well as a benzoyl, palmitoyl, cyclopropane-carbonyl, $C_{1-5}$ alkylcarbamoyl or phenylcarbamoyl group; and the dotted lines represent valence bonds optionally being present, with the proviso that no double bond exists between the N(3) and C(4) atoms when both $R^3$ and $R^4$ stand for hydrogen, and their stereoisomers as well as acid addition salts (where possible) and pharmaceutical compositions containing these compounds.

The compounds of-general formula (I) according to the invention have an asymmetric molecular structure. The general formula (I) relates to all possible individual stereoisomers and their mixtures.

According to an other aspect of the invention, there is provided a process for the preparation of the new compounds of general formula (I) and the acid-addition salts thereof.

The aim of the present invention is to develop new compounds of the general formula (I) which possess valuable central nervous system (CNS), particularly muscle-relaxant and/or anticonvulsive, activity. A single compound showing such effect is only known among 2,3-benzodiazepines, namely 1-(4-aminophenyl)-4-methyl-7,8-methylenedioxy-5H-2,3-benzodiazepine (United States patent specification No. 4,614,740) also prepared by the authors of the present invention. In the course of detailed pharmacological screening it was revealed, however, that the above compound was positive in the Ames-test, i.e. it proved to be mutagenic. Thus, it is the specific aim of the present invention to find out novel 2,3-benzodiazepine derivatives which retain their valuable muscle-relaxant and anticonvulsive activity but are negative in the Ames test.

The new compounds of general formula (I), wherein R, $R^1$, $R^2$, $R^3$, $R^4$ and the dotted lines are as defined above, and their pharmaceutically acceptable acid-addition salts completely satisfy this requirement.

According to the invention, the compounds of general formula (I) are prepared by a) acylating a compound of formula (II)

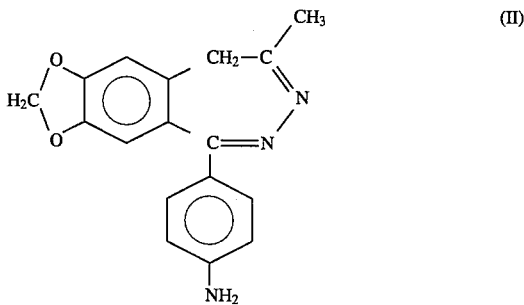

with a $C_{1-6}$ aliphatic carboxylic acid optionally substituted,by a methoxy, cyano, carboxyl or phenyl group or by one or more halogen(s); or with benzoic, cyclopropanecarboxylic or palmitic acid or with a reactive derivative thereof; and, if desired, reacting a new compound of general formula (I) thus obtained, wherein $R^4$ means a $C_{1-6}$-alkanoyl group substituted by a halogen, with a $C_{1-4}$ alkylamine, di($C_{1-4}$ alkyl)amine or pyrrolidine, to obtain compounds of the general formula (1), wherein $R^2$, $R^3$ and the dotted lines are as defined above, $R^4$ means a $C_{1-6}$ alkanoyl group optionally substituted by a methoxy, cyano, carboxy, phenyl-$C_{1-4}$ alkyl-amino, di($C_{1-4}$ alkyl)amino or pyrrolidino group or one or more halogen(s); or a benzoyl, cyclopropane-carbonyl or palmitoyl group; R and $R^1$ are absent and a double bond is present between the N(3) and C(4) atoms;

b) acylating a compound of the general formula (III),

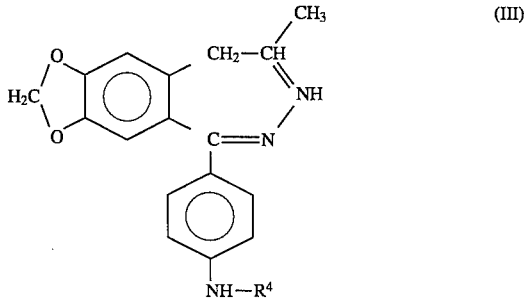

wherein $R^4$ is as defined above, with a $C_{1-6}$ aliphatic carboxylic acid optionally substituted by a methoxy, cyano, carboxy or phenyl group or by one or more halogen(s); or with benzoic or cyclopropanecarboxylic acid or with a reactive derivative thereof; and, if desired, reacting a new compound of general formula (I) thus obtained, wherein $R^4$ means a $C_{1-6}$ alkanoyl group substituted by a halogen, with a $C_{1-4}$ alkyl-amine, di($C_{1-4}$ alkyl)amine or pyrrolidine, to obtain compounds of the general formula (I), wherein $R^1$, $R^2$, $R^3$, $R^4$ and the dotted lines are as defined above, R means a $C_{1-6}$ alkanoyl group optionally substituted by a methoxy, cyano, carboxy, phenyl, $C_{1-4}$ alkylamino, di($C_{1-4}$ alkyl)amino or pyrrolidino group or one or more halogen(s); or a benzoyl or a cyclopropanecarbonyl group; and no double bond exists between the N(3) and C(4) atoms; or c) acylating a compound of formula (II) with an N-phthaloylamino acid of the general formula (VI),

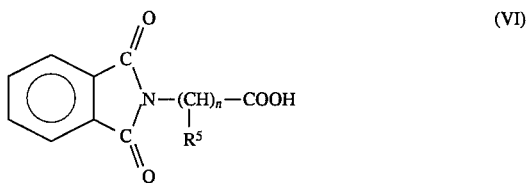

wherein $R^5$ stands for hydrogen or a $C_{1-4}$ alkyl group and n is 1 in case of α-amino acids, whereas $R^5$ means hydrogen and n is an integer of 2 to 5 in case of β-ε amino acids, and, if desired, removing the phthaloyl group, to obtain compounds of the general formula (I), wherein $R^2$ and the dotted lines are as defined above, $R^3$ means hydrogen, $R^4$ stands for a $C_{1-6}$ alkanoyl group substituted by an amino or phthalimido group, both R and $R^1$ are absent, and a double bond is present between the N(3) and C(4) atoms; or d) acylating a compound of the general formula (III), wherein $R^4$ is as defined above, with an N-phthaloylamino acid of the general formula (VI), wherein $R^5$ stands for hydrogen or a $C_{1-4}$ alkyl group and n is 1 in case of α-amino acids, whereas $R^5$ means hydrogen and n is an integer of 2 to 5 in case of β-ε amino acids, and, if desired, removing the phthaloyl group, to obtain compounds of the general formula (I), wherein $R^1$, $R^2$ and the dotted lines are as defined above, $R^3$ means hydrogen, $R^4$ is as defined above except hydrogen, R stands for a $C_{1-6}$ alkanoyl group substituted by an amino or phthalimido group and no double bond is present between the N(3) and C(4) atoms; or e) reacting a compound of the formula (II) with a $C_{1-5}$ alkyl isocyanate or phenyl isocyanate, to obtain compounds of the general formula (I), wherein $R^2$ and the dotted lines are as defined above, $R^3$ means hydrogen, $R^4$ represents a $C_{1-5}$ alkylcarbamoyl or phenylcarbamoyl group, R and $R^1$ are absent and a double bond is present between the N(3) and C(4) atoms; or f) reacting a compound of the general formula (III), wherein $R^4$ is defined as above, with a $C_{1-5}$ alkyl isocyanate or phenyl isocyanate, to obtain compounds of the general formula (I), wherein $R^1$, $R^2$ and the dotted lines are as defined above, $R^3$ means hydrogen, $R^4$ is as defined above except hydrogen, R stands for a $C_{1-5}$ alkylcarbamoyl or phenylcarbamoyl group and no double bond is present between the N(3) and C(4) atoms; or g) selectively reducing a nitro compound of the formula (IV)

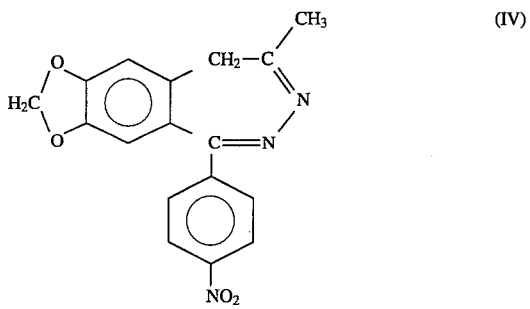

to a novel compound of the general formula (V)

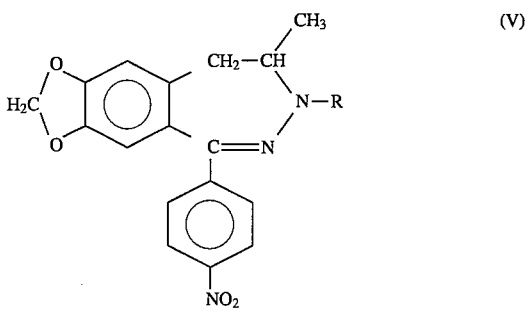

wherein R means hydrogen, then either acylating the compound of general formula (V) thus obtained by using any of the above processes b), d) or f) and reducing the nitro group of the thus-obtained new compound of general formula (V), wherein R is as defined above, to an amino group, or first reducing the nitro group and then acylating the compound of general formula (III) thus obtained, wherein $R^4$ stands for hydrogen, by using any of the above processes b), d) or f), to obtain compounds of the general formula (I), wherein $R^1$, $R^3$ and $R^4$ represent hydrogen, $R^2$, R and the dotted lines are as defined above and no double bond is present between the N(3) and C(4) atoms; or acylating a new compound of the general formula (I), wherein R, $R^1$, $R^2$ and the dotted lines are as defined above, $R^3$ and $R^4$ mean hydrogen and no double bond is present between the N(3) and C(4) atoms, with a $C_{1-6}$ aliphatic carboxylic acid optionally substituted by a methoxy, cyano or carboxy group or by one or more halogen(s); or with benzoic acid; or with a reactive derivative thereof, to obtain compounds of the general formula (I), wherein $R^1$, $R^2$, $R^3$ and the dotted lines are as defined above, R and $R^4$ represent a $C_{1-6}$-alkanoyl group optionally substituted by a methoxy, cyano or carboxy group, or by one or more halogen(s); or a benzoyl group; and no double bond is present between the N(3) and C(4) atoms; or i) reacting a new compound of the general formula (I), wherein R, $R^1$, $R^2$ and the dotted lines are as defined above, $R^3$ and $R^4$ mean hydrogen and no double bond is present between the N(3) and C(4) atoms, with a $C_{1-5}$ alkyl isocyanate or phenyl isocyanate, to obtain compounds of the general formula (I), wherein $R^1$, $R^2$ and the dotted lines are as defined above, R stands for a $C_{1-6}$ alkanoyl group optionally substituted by a methoxy, cyano or carboxy group, or by one or more halogen(s); or a benzoyl group; $R^3$ stands for hydrogen; $R^4$ represents a $C_{1-5}$ alkylcarbamoyl or phenylcarbamoyl group and no double bond is present between the N(3) and C(4) atoms; or j) acylating a new compound of the general formula (I), wherein $R^1$, $R^2$ and the dotted lines are as defined above, $R^3$ and $R^4$ mean hydrogen and no double bond is present between the N(3) and C(4) atoms, with an N-phthaloylamino acid of the general formula (VI), wherein $R^5$ stands for hydrogen or a $C_{1-4}$ alkyl group and n is 1 in case of α-amino acids, whereas $R^5$ means hydrogen and n is an integer of 2 to 5 in case of β-ε amino acids, and, if desired, removing the phthaloyl group, to obtain compounds of the general formula (I), wherein $R^1$, $R^2$ and the dotted lines are as defined above, R represents a $C_{1-6}$ alkanoyl group optionally substituted by a methoxy, cyano or carboxy group or by one or more halogen(s); or a benzoyl group; $R^3$ stands for hydrogen, $R^4$ represents a $C_{1-6}$ alkanoyl group substituted by an amino or phthalimido group and no double bond is present between the N(3) and C(4) atoms, and, if desired, transforming a base of the general formula (I), obtained by any of the above processes a) to j), to an acid-addition salt.

According to a preferred embodiment of the process of the present invention the acylation of the compounds of the general formulae (I), (II), (III) and (V) can be carried out preferably with a suitable carboxylic acid, in the presence of dicyclohexyl-carbodiimide in a suitable solvent, preferably in dichloromethane, in a temperature range of 10 to 30 °C. during 1 to 25 hours.

According to an other preferred embodiment of the present invention the compounds of the general formulae (I), (II), (III) and (V) can be acylated in a temperature range of zero to 150° C. by a suitable reactive acyl derivative, i.e. carboxylic acid anhydride, mixed anhydride or acyl chloride, in the absence or presence of a solvent usually applied in acylations of such types such as chloroform or dichloromethane, in the absence or presence of an acid-binding agent, such as triethylamine. If the additive acylation is performed with isocyanates, the reaction is advantageously carried out in dimethylformamide, benzene or dichloromethane in a temperature range of 15° to 100° C. during 0.5 to 100 hours.

The selective reduction of the compound of general formula (IV) to the compound of general formula (V), wherein R denotes a hydrogen atom, can be performed by an inorgaic or inorganic-organic complex metal hydride, preferably sodium borohydride, in a solvent or solvent mixture which has no or only low reactivity to the complex metal hydride applied. In these reactions a $C_{1-4}$ alcohol or pyridine is the solvent of choice. (Similar selective reductions are described in the U.S. Pat. Nos. 4,423,044 and 4,835,152.)

The nitro group of the new compounds of general formula (V) are reduced to an amino group by hydrazine or hydrazine hydrate in the presence of a catalyst such as palladium, platinum or Raney nickel in a $C_{1-4}$ alcohol, dioxane, tetrahydrofuran, benzene, dimethylformamide, dimethylacetamide or in a mixture thereof.

According to a preferred embodiment of the process of the present invention the reduction can be carried out in methanol by hydrazine or hydrazine hydrate in the presence of Raney nickel catalyst in a temperature range of 10° to 65 ° C. (U.S. Pat. No. 4,614,740) but, if desired, the reduction and the removal of the phthaloyl protecting group described in process d) can be performed in the same vessel.

The N-phthaloylamino acids of the general formula (IV) containing a chiral carbon atom, wherein $R^5$ means a $C_{1-4}$ alkyl group and n is 1, can be prepared from DL-, L- and/or D-alpha-amino acids.

The compounds of the general formula (I) of the invention, which contain a basic amino group, wherein $R^3$ and $R^4$ mean a hydrogen atom or R and/or $R^4$ stand for an aminoacyl group, can be transformed to their acid-addition salts by known methods.

The preparation of the compounds of the general formula (II) used as starting materials in the process of the present invention is described in the U.S. Pat. No. 4,614,740, that of the compound of the general formula (III), wherein $R^4$ stands for a hydrogen atom, in the U.S. Pat. No. 4,835,152, while that of the compound of general formula (IV) is published in the French patent specification No. 85,09793. The compounds of general formula (III), wherein $R^4$ stands for various acyl grups, are new. The process for their preparation is described hereinafter, before Table 10, or they can be synthetized by methods described therein. The preparation of the new starting compounds of the general formula (V) is described in the Examples. The (α-ε)-amino acid derivatives of general formula (VI) are prepared by methods known from the literature [J. Am. Chem. Soc. 35, 1133 (1913); 41, 845 (1919); Berichte der Deutschen Chemischen Gesellschaft 40, 498, 2649 (1907); 46, 103, 3159 (1913); 47, 3166 (1914)] or by known methods using the reaction of phthalimide potassium with the required halo-carboxylic acid.

Preferably, the selective reduction of the compound of the formula IV to the compound of the general formula V, wherein R stands for a hydrogen atom, can be performed stereoselectively to produce either the (−) or (+) enantiomer. This enantioselective reduction uses a chiral hydride reagent, such as a chiral borane derivative. These chiral boranes are generally produced by the reaction of borane ($BH_3$) with a chiral 1,2-aminoalcohol. These preferred chiral boranes are prepared by the reaction of borane with 2-amino-3-methyl-1,1-diphenylbutan-1-ol, 2-amino-4-methyl-1,1-diphenylpentan-1-ol, or 2-amino-3-methyl-1,1-diphenylpentan-1-ol, that are readily prepared from valine, leucine, and isoleucine, respectively. See Itsuno, et al., *J. Chem. Soc., Perkin Trans.*, 1, 2039,(1985). The most preferred chiral 1,2 -aminoalcohol is (−) or (+)-2-amino-4-methyl-1,1 -diphenylpentan-1-ol. The (+)-enantiomer of the formula V compound is prepared using the chiral boranes derived from D-valine, D-leucine, or D-isoleucine. Similarly, the (−)-enantiomer of the formula V compound is prepared using the chiral boranes derived from L-valine, L-leucine, or L-isoleucine. The reaction is typically carried out under an atmosphere of dry nitrogen in an organic solvent, such as dry dichloromethane or dry 1,2-dichloroethane, at a temperature of about 25° C. to about 60° C. When the reaction is carried out in 1,2-dichloroethane at 60° C., using 1.5 equivalents of the chiral borane reagent, the reaction is complete after about 3 hours.

The compounds of the general formula (I) prepared by the process of the present invention possess central nervous system (CNS) activity, such as anticonvulsive, muscle-relaxant and neuroprotective effects, which can be shown by pharmacological tests.

In the comparative study 1-(4-aminophenyl)-4-methyl-7,8-methylenedioxy-5H-2,3-benzodiazepine (U.S. Pat. No. 4,614,740, in the following "reference compound"), having similar structure and efficacy as the compounds of the invention, was applied as reference compound. As already mentioned in the introduction, this compound proved to be Ames-positive in addition to its valuable pharmacological properties. In opposition to this the compounds of the present invention proved to be negative in the Ames-test.

The pharmacological effects of the compounds of general formula (I) are presented in Tables 1 to 8.

Narcosis-potentiating effect in mice

The narcosis-potentiating effect was tested with 3 oral doses in 10 mice/dose. The $ED_{50}$ value is the dose prolonging the narcosis period induced by 50 mg/kg of i.v. sodium hexobarbital to its twofold value in 50% of the animals in comparison to the control group treated only with the vehicle. The $ED_{50}$ values were calculated by the Litchfield-Wilcoxon method [J. Pharmacol. Exp. Ther. 96, 99 (1949)]. The results are presented in Table 1.

TABLE 1

| Narcosis potentiating effect in mice | |
|---|---|
| Compound Example No. | $ED_{50}$ p.o. mg/kg |
| Reference compound | 7.4 |
| 15 (16) | 3.6 |
| 18 | 8.8 |
| 39 | 27.5 |
| 42 | 7.9 |
| 44 | 13.5 |
| 44 | 13.5 |
| 45 | 4.9 |
| 46 | 11.5 |
| 48 | 5–8 |
| 49 | 9.5 |
| 56 | 12.5–25 |
| 60 | 4.4 |
| 62 | 5.2 |
| 66 | 24.0 |
| 69 | 15–20 |
| 73 | 4.5 |
| 98 | 5.8 |
| 107 | 6.25–12.5 |
| 108 | ≈12.5 |
| 109 | ≈12.5 |
| 115 | 7.7 |

The data of Table 1 demonstrate that the efficacy of several compounds is similar or significantly superior to that of the reference compound. Compounds of Examples 15 (16), 45, 60, 73 and 98 proved to be especially potent.

Anticonvulsive effect in mice

The anticonvulsive effec of the compounds was measured by using the electroshock test [Swinyard: J. Pharmacol. Exp. Ther. 106, 319 (1952)], furthermore by using various chemical agents such as pentetrazole [Goodman: J. Pharmacol. Exp. Ther. 108, 168 (1953)], strychnine [Roskovski: J. Pharmacol. Exp. Ther. 129, 75 (1960)], bemegride, nicotine and 4-amino-pyridine. The test compounds were orally administered in 3 doses, to 10 male CFLP mice per dose.

The results are presented in Table 2.

TABLE 2

| | Anticonvulsive effect in mice | | | | | |
|---|---|---|---|---|---|---|
| Compound Example No. | ES | Pentetrazole | Strychnine $ED_{50}$ p.o. mg/kg | Bemegride | Nicotine | 4-AP |
| Reference compound | 38 | 115 | 87 | 73 | 70 | 43 |
| 15 (16) | 12.5 | 37 | >200 | 16 | 45 | 9 |
| 18 | 17.5 | 29 | | | | |
| 39 | 53 | 170 | >200 | >200 | >200 | 29 |
| 42 | 24 | 33 | 28 | 24 | 155 | 34 |

TABLE 2-continued

| | Anticonvulsive effect in mice | | | | | |
|---|---|---|---|---|---|---|
| Compound Example No. | ES | Pentetrazole | Strychnine $ED_{50}$ p.o. mg/kg | Bemegride | Nicotine | 4-AP |
| 45 | 27 | 44 | >100 | 51 | 30–80 | ≈70 |
| 46 | 20 | 57 | >100 | 70–80 | ≈100 | 25–30 |
| 48 | 10.5 | 35–40 | | | | |
| 49 | 25 | 53 | >100 | 30–35 | 45 | 28 |
| 60 | 24 | 62 | | | | |
| 62 | 12.5 | 56 | 25–50 | | | |
| 66 | 42 | 135 | ≈100 | >100 | 100–150 | 84 |
| 69 | 57 | >100 | | | | |
| 73 | 16 | 62 | 50–100 | 49 | 53 | 25 |
| 98 | 8.4 | 19 | 20 | 11 | 19 | 13.5 |
| 107 | 23.5 | 120 | | | | |
| 108 | 27 | >100 | | | | |
| 109 | 21 | >100 | | | | |
| 115 | 17.1 | 23.9 | | | | |

ES = electroshock
4-AP = 4-aminopyridine

The above data demonstrate that the anticonvulsive effect of several test compounds (of Examples 15, 42, 45, 46, 73, 98, 107, 108, 109 and 115) is superior to that of the reference compound.

Muscle-relaxant activity in mice

The muscle-relaxant activity was measured in two tests. In Randall's inclined screen test [J. Pharmacol. Exp. Ther. 129, 163 (1960)] the compounds were applied in 3 i.p. doses to 10 CFLP mice per dose. The results are shown in Table 3.

TABLE 3

| Inclined screen test in mice | |
|---|---|
| Compound Example No. | $ED_{50}$ i.p. mg/kg |
| Reference compound | 47 |
| 15 (16) | 23.5 |
| 18 | 31 |
| 42 | 42 |
| 45 | 35 |
| 48 | 20.5 |
| 49 | 36 |
| 60 | 150 |
| 62 | 25 |
| 66 | 52 |
| 73 | 27 |
| 98 | 18.0 |
| 107 | >200 |
| 108 | >200 |
| 109 | 61 |
| 115 | 16.1 |

The rotarod test was used to measure muscular tone and motor coordination [Dunham and Miya: J. Am. Pharm. Assoc. 46, 208 (1957)]. The results obtained with the three selected compounds of highest activity and that of the reference compound are presented in Table 4.

TABLE 4

Rotarod test in mice

| Compound Example No. | $ED_{50}$ i.p. mg/kg |
|---|---|
| Reference compound | 24 |
| 15 (16) | 3.7 |
| 42 | 8.1 |
| 98 | 8.6 |

Tables 3 and 4 demonstrate that several compounds possess strong muscle-relaxant activity (compounds of Examples 15, 18, 42, 45, 48, 49, 62, 73, 98 and 115).

Effect on spinal function

The effect on spinal function was studied with the most active compound (compound of Example 15 or 16) and the reference compound. Table 5 shows the effect on polysynaptic flexor reflexes in cats [Farkas and Kárpáti: Pharm. Res. Comm. 20, S1, 141 (1988)].

TABLE 5

Effect on spinal flexor reflex

| Compound Example No. | Cumulative doses mg/kg, i.v. | Inhibition of flexor reflex in percent of control | $ED_{50}$ mg/kg |
|---|---|---|---|
| Reference compound | 0.25 | 12 | 0.90 |
|  | 0.5 | 30 | (0.46–1.76) |
|  | 1.0 | 57 |  |
|  | 2.0 | 77 |  |
| 15 (16) | 0.05 | 11 | (0.19–0.62) |
|  | 0.1 | 19 |  |
|  | 0.2 | 31 |  |
|  | 0.4 | 52 |  |
|  | 0.8 | 77 |  |

The effect of the above compounds on the spinal root potentials in cats was tested in spinally immobilized animals Farkas et al.: Neuropharmacology 21, 161 (1989)].

The results are presented in Table 6.

TABLE 6

Effect on spinal root potentials in cats

| Compound Example No. | Cumulative i.v. doses mg/kg | Monosynaptic reflex | Polysynaptic reflex | Dorsal root reflex | Dorsal root potential |
|---|---|---|---|---|---|
| Reference compound | 0.5 | 16 | 15 | 0 | 2 |
|  | 1.0 | 27 | 24 | 2 | 4 |
|  | 2.0 | 47 | 43 | 4 | 4 |
| 15 (16) | 0.1 | 10 | 8 | 1 | 1 |
|  | 0.2 | 10 | 16 | 3 | 2 |
|  | 0.4 | 32 | 29 | 5 | 4 |
|  | 0.8 | 56 | 51 | 11 | 8 |
|  | 1.4 | 78 | 73 | 14 | 14 |

Monosynaptic reflex-inhibiting $ED_{50}$ values:
Reference compound: 2.20 (1.02–4.75) mg/kg, i.v.
Compound No. 15 (16): 2.30 (1.06–5.01) mg/kg, i.v.
Polysynaptic reflex-inhibiting $ED_{50}$ values:
Reference compound: 0.60 (0.32–1.13) mg/kg, i.v.
Compound No. 15 (16): 0.73 (0.39–1.37) mg/kg, i.v.

Electrophysiological tests

The inhibitory effects on the field potentials induced by electric stimulation in surviving rat neocortex slices in vitro [Fletcher et al., Br. J. Pharmacology 95, 585 (1988)] are summarized in Table 7.

TABLE 7

Inhibition of field potentials induced in rat neocortex slices

| Compound Example No. | Concentration μm | Inhibition of induced field potentials in % of control | $IC_{50}$ μM |
|---|---|---|---|
| Reference compound | 10 | 22 | 30.0 |
|  | 20 | 39 |  |
|  | 40 | 62 |  |
|  | 80 | 73 |  |
| 15 (16) | 10 | 30 | 21.5 |
|  | 20 | 47 |  |
|  | 40 | 69 |  |
|  | 80 | 82 |  |

The non-NMDA (quisqualate) antagonist effect was tested in rat neocortex slices by using the method of Harrison and Simmonds [Br. J. Pharmacol. 84, 381 (1981)]. In rat neocortex slices the DC-potential changes induced by quisqualate perfusion were dose-dependently inhibited by the reference compound in the concentration range of 10–50 μM. At the concentration defined, the compound of Example 15 (16) proved to be twice as active as the reference compound in inhibiting the response to the 2-minute perfusion with 10 μM of quisqualate. However, both molecules failed to affect the responses induced by NMDA. Accordingly, the compound of Example 15 (16) can be considered to be a selective, non-NMDA but quisqualate-type excitatory amino acid antagonist.

Acute toxicity in rats

Acute toxicity data obtained in rats are summarized in Table 8.

TABLE 8

Acute toxicity in rats

| Compound Example No. | Sex | Route of administration | $LD_{50}$ mg/kg |
|---|---|---|---|
| 15 (16) | Male | i.p. | 145 (128–163.1) |
|  | Male | p.o. | ≈200 |
|  | Female | i.p. | 140 (122–161) |
|  | Female | p.o. | 235 (190–291) |
| 42 | Male | i.p. | 155 (109.9–218.5) |
|  | Male | p.o. | >600 |
|  | Female | i.p. | 180 (156.5–207.0) |
|  | Female | p.o. | >600 |

Acute toxicity in rats

At toxic dose levels the compounds induced a dose-dependent muscle tone reduction, ataxia, adynamia, and loss of the righting reflex. The cause of mortality was respiratory insufficiency developing within 1 to 2 hours after i.p. administration and within 10 to 20 hours after oral application.

Based on the above pharmacological results, the compounds of general formula (I) according to the invention possess significant anticonvulsive, muscle-relaxant and excitatory amino acid-antagonist (neuroprotective) effects. Thus, they are therapeutically useful for the treatment of epilepsy as well as various diseases connected with spasms of the skeletal musculature and cerebral ischaemia (stroke).

The invention also relates to pharmaceutical compositions containing compounds of general formula (I) or pharmaceutically acceptable acid-addition salts thereof as active ingredients as well as to the preparation of these compositions.

For therapeutical use, the active compounds according to the invention are suitably formulated to pharmaceutical compositions by admixing them with commonly used non-toxic, inert, solid or liquid pharmaceutical carriers and/or auxiliary materials useful for enteral or parenteral administration. As carriers, e.g. water, gelatine, lactose, starch, pectin, magnesium stearate, stearic acid, talc or vegetable oils can be used. As auxuliary materials, e.g. preservatives and wetting as well as emulsifying, dispersing and aromatizing agents and buffers can be employed.

By using the above-mentioned carriers and auxiliary materials, the active agents of the invention may be transformed to the usual pharmaceutical compositions, e.g. to solid compositions (such as tablets, capsules, pills or suppositories) or liquid compositions (such as aqueous or oily sulutions, suspensions, emulsions or syrups) as well as to injectable solutions, suspensions or emulsions.

For therapeutical purposes, the daily dose of the compounds of the invention amounts commonly to 0.2–1.5 mg/kg of body weight which is administered daily, optionally divided to several doses.

Based on the above facts, the present invention also provides:
a method of blocking one or more excitatory amino acid receptors in mammals. This method comprises administering to a mammal in need of such treatment a pharmaceutically effective amount of the general formula (I);
a method of treating epilepsy in mammals. This method comprises administering to the mammal in need of such treatment an antiepileptic amount of a compound of the general formula (I);
a method of treating spasms of the skeletal musculature in mammals. This method comprises administering to the mammal in need of such treatment a muscle-relaxing amount of a compound of the general formula (I);
a method of treating cerebral ischaemia (stroke) in mammals. This method comprises administering to the mammal in need of such treatment a pharmaceutically effective amount of a compound of the general formula (I).

The compounds prepared by the process of the invention were identified by elementary analysis, their purity and structure were controlled and confirmed by thin-layer chromatography, IR, $^1$H-NMR, $^{13}$C-NMR and mass spectrometry.

The invention is illustrated in detail by the following non-limiting Examples.

EXAMPLE 1

1-(4-Diacetylaminophenyl)-3-acetyl-4-methylene-7,8-methylenedioxy-4,5-dihydro-3H-2,3-benzodiazepine 2.93 g (0.01 mol) of 1-(4-aminophenyl)-4-methyl-7,8-methylenedioxy-5H-2,3-benzodiazepine were refluxed with 20 ml of acetic anhydride for 6 hours. The solution was evaporated at reduced pressure, the residue was taken up in 2×20 ml of anhydrous ethanol, the solution was repeatedly evaporated and the resulting residue of 4.55 g was submitted to column chromatography (adsorbent: Kieselgel 60, eluant: ethyl acetate—benzene 4:1). The raw product was triturated with 20 ml of hot isopropanol to yield 1.44 g (34.4 %) of the aimed product, m.p. 240°–245° C. (slight decomp.).
$C_{23}H_{21}N_3O_5$=419.445

EXAMPLE 2

1-(4-Formylaminophenyl)-4-methyl-7,8-methylenedioxy-5H-2,3-benzodiazepine 3.0 g (10.2 mmol) of 1-(4-aminophenyl)-4-methyl-7,8-methylenedioxy-5H-2,3-benzodiazepine were dissolved in 160 ml of dichloromethane and first 2.75 g (13.3 mmol) of dicyclohexylcarbodiimide, then 0.51 ml (13.3 mmol) of 100 % formic acid were added and the reaction mixture was stirred for 2 hours at room temperature. The precipitated N,N'-dicyclohexylurea was filtered, the filtrate was exracted with 2×30 ml of 10 % aqueous sodium carbonate solution, then with 2×30 ml of distilled water, the organic layer was dried and evaporated at reduced pressure. The residue was dissolved in ethyl acetate, filtered and evaporated under reduced pressure. The resulting raw product was recrystallized from 20 ml of 50 % ethanol to yield 2.93 g (89.3 %) of the aimed product, m.p. 152°–154° C. (slight decomp.).
$C_{18}H_{15}N_3O_3$=321.342

EXAMPLES 3 to 7

The compounds of Examples 3 to 7 were prepared by the process described in Example 2.

EXAMPLE 3

1-(4-Cyanoacetylaminophenyl)-4-methyl-7,8-methylene-dioxy-5H-2,3-benzodiazepine $C_{20}H_{16}N_4O_3$=360.380, m.p.: 241°–243° C. (decomp.).

EXAMPLE 4

1-(4-Methoxyacetylaminophenyl)-4-methyl-7,8-methylene-dioxy-5H-2,3-benzodiazepine $C_{20}H_{19}N_3O_4$=365.396, m.p.: 203°–205 ° C.

EXAMPLE 5

1-(4-Valerylaminophenyl)-4-methyl-7,8-methylene-dioxy-5H-2,3-benzodiazepine $C_{22}H_{23}N_3O_3$=377.450, m.p.: 217°–219° C. (decomp.).

EXAMPLE 6

1-(4-Phenylacetylaminophenyl)-4-methyl-7,8-methylene-dioxy-5H-2,3-benzodiazepine $C_{25}H_{21}N_3O_3$=411.467, m.p.: 245°–247° C. (decomp.).

EXAMPLE 7

1-(4-Cyclopropanecarbonylaminophenyl)-4-methyl-7,8-methylenedioxy-5H-2,3-benzodiazepine $C_{21}H_{19}N_3O_3$=361.407, m.p.: 260°–262° C. (decomp.).

EXAMPLE 8

1-(4-Acetylaminophenyl)-4-methyl-7,8-methylenedioxy-5H-2,3-benzodiazepine 10 g (34 mmol) of 1-(4-aminophenyl)-4-methyl-7,8 -methylenedioxy-5H-2,3-benzodiazepine were stirred for 3 hours with 100 ml of acetic anhydride. The crystals formed were filtered, washed with 5×10 ml of anhydrous ethanol and dried, yielding 9.2 g of raw product, m.p. 252°–254 ° C. (decomp.). This product was treated with 45 ml of hot 99.5 % ethanol. After cooling the crystals were filtered, washed with 3×10 ml of ethanol and dried to give 8.68 g (76.1%) of the aimed product, m.p.: 256°–258° C. (decomp.).
$C_{19}H_{17}N_3O_3=335.369$

EXAMPLE 9

1-(4-Propionylaminophenyl)-4-methyl-7,8-methylenedioxy-5H-2,3-benzodiazepine $C_{20}H_{19}N_3O_3=349.396$, m.p.: 228°–230° C. (decomp.).
It was prepared by the process described in Example 8.

EXAMPLE 10

1-(4-Pivaloylaminophenyl)-4-methyl-7,8-methylenedioxy-5H-2,3-benzodiazepine 1.56 ml (11.2 mmol) of triethylamine and 1.38 ml (11.2 mmol) of pivaloyl chloride were added to a solution of 3 g (10.2 mmol) of 1-(4-aminophenyl)-4-methyl-7,8 -methylenedioxy-5H-2,3-benzodiazepine in 160 ml of dichloromethane and the reaction mixture was stirred at 25° C. for one hour. The precipitate formed was filtered, washed with 3×5 ml of dichloromethane, then with 3×20 ml of water and dried to yield 1.59 g of pure product, m.p. 225°–227° C. (decomp.). The other portion of the product was isolated from the organic phase. The filtrate was extracted with 3×20 ml of water, then with 3×15 ml of 4% aqueous sodium hydroxide solution, finally with 2×30 ml of water. The organic layer was subsequently dried and evaporated under reduced pressure. The crystalline residue was combined with the former product of 1.59 g and suspended in 20 ml of hot ethanol. The product was filtered after cooling, washed with 3×3 ml of ethanol and dried to yield 3.38 g (87.8 %) of the pure product, m.p.: 225°–227° C. (decomp.).
$C_{22}H_{23}N_3O_3=377.450$

EXAMPLE 11

1-(4-Benzoylaminophenyl)-4-methyl-7,8-methylenedioxy-5H-2,3-benzodiazepine 1.0 ml (15 mmol) of benzoyl chloride and 2.1 ml (15 mmol) of triethylamine were added to a solution of 4 g (13.6 mmol) of 1-(4-aminophenyl)-4-methyl-7,8-methylenedioxy-5 H-2,3-benzodiazepine in dichloromethane and the reaction mixture was stirred at 25° C. for 24 hours. The solution was extracted with 3×30 ml of water, 3×20 ml of a 4% aqueous sodium hydroxide solution and finally with 2×30 ml of distilled water. The organic layer was dried, evaporated under reduced pressure, then the crystalline residue was treated with 20 ml of hot ethanol to obtain 3.97 g of raw product, m.p. 242°–243° C. This raw product was repeatedly treated with 20 ml of hot ethanol, next day it was filtered at 0°–5° C., washed with 3×3 ml of ethanol and dried at 100° C. to yield 3.85 g (71.3 %) of the pure aimed product, m.p. 246°14 247° C. (decomp.).
$C_{24}H_{19}N_3O_3=397.40$

EXAMPLE 12

1-(4-Palmitoylaminophenyl)-4-methyl-7,8-methylenedioxy-5H-2,3-benzodiazepine By following the process described in Example 11, with recrystallization of the raw product from 50% ethanol, the pure aimed product was obtained, m.p. 138°–140° C.
$C_{33}H_{45}N_3O_3=531.747$

EXAMPLE 13

1-(4-Phenylcarbamoylaminophenyl)-4-methyl-7,8-methylenedioxy-5H-2,3-benzodiazepine 0.22 ml (2.04 mmol) of phenyl isocyanate was added to a solution of 0.50 g (1.7 mmol) of 1-(4-aminophenyl)-4 -methyl-7,8-methylenedioxy-5H-2,3-benzodiazepine in 4 ml of dimethylformamide and the reaction mixture was stirred at 25 ° C. for one hour. Then it was diluted with 20 ml of diethyl ether and filtered at 5° C. The crystals were washed with 2×5 ml of diethyl ether and dried at 60°–100° C. The resulting 0.70 g of raw product, m.p. 239°–240° C. (sintering at 180° C.) was refluxed in 15 ml of ethanol, filtered after cooling, washed wtih 3×1 ml of ethanol and dried at 100° C. to yield 0.55 g (78.6%) of the aimed product, m.p. 240°–241° C. (decomp.).
$C_{24}H_{20}N_4O_3=412.456$

EXAMPLE 14

1-[4-(4-Carboxybutyrylamino)phenyl]-4-methyl-7,8-methylenedioxy-5H-2,3-benzodiazepine A solution of 0.50. g (1.7 mmol) of 1-(4-aminophenyl)-4 -methyl-7,8-methylenedioxy-5H-2,3-benzodiazepine in 30 ml of anhydrous dichloromethane was stirred with 0.18 g (1.87 mmol) of glutaric acid anhydride at 20°–25° C. for 6 hours. Next day the crystals formed were filtered at 0°–5° C., washed with 3×2 ml of dichloromethane and dried at 60°–80° C. to give 0.60 g (87.0%) of the pure aimed product, m.p. 225°–227° C. (decomp.).
$C_{22}H_{21}N_3O_5=407.434$

EXAMPLE 15

1-(4-Aminophenyl)-3-acetyl-4-methyl-7,8-methylenedioxy-5H-2,3-benzodiazepine To a solution of 3.58 g (12.1 mmol) of 1-(4 -aminophenyl)-4-methyl-7,8-methylenedioxy-3,4-dihydro-5H-2,3 -benzodiazepine in 100 ml of chloroform first 1.68 ml (12.1 mmol) of triethylamine, then under constant ice-cooling and stirring 1.15 ml (12.1 mmol) of acetic anhydride were added. Stirring was continued for additional 2 hours, then the solution was extracted with 3×100 ml of water, the organic layer was dried and evaporated under reduced pressure. The crystalline residue was recrystallized from 40 ml of isopropanol to obtain 3.50 g (85.7 %) of the aimed product, m.p. 220°–222 ° C. After repeated recrystallization the m.p. increased to 223°–225° C.
$C_{19}H_{19}N_3O_3=337.385$
Hydrochloride: $(C_{19}H_{20}N_3O_3)Cl=373.850$, m.p.: 248°–252° C. (decomp.).

EXAMPLE 16

1-(4-Aminophenyl)-3-acetyl-4-methyl-7,8-methylene-dioxy-3,4-dihydro-5H-2,3-benzodiazepine To a suspension of 1.91 g (5.37 mmol) of 1-(4 -nitrophenyl)-3-acetyl-4-methyl-7,8-methylenedioxy-3,4 -dihydro-5H-2,3-benzodiazepine (product of Example 27) in 40 ml of methanol about 0.2 g of Raney nickel catalyst and 1.4 ml (28 mmol) of 100% hydrazine hydrate were added, then the reaction mixture was stirred at 20°–25° C. for one hour. The starting nitro derivative was dissolved within 10–20 minutes. After filtering the filtrate was evaporated under reduced pressure, the white crystalline residue was washed with 30 ml of distilled water onto a filter, it was washed with 3×10 ml of distilled water and dried at 100° C. to give 1.50 g of a raw product, m.p. 218°–220° C. This raw product was purified by treating with 12 ml of hot isopropanol. After cooling it was filtered at 5° C., washed with 3×1 ml of isopropanol and dried at 100° C. to yield 1.40 g (77.35%) of a white crystalline powder, m.p. 221°–223° C. On the basis of analyses and spectra it was identical to the product of Example 15 obtained by a different process.

EXAMPLE 17 to 25

The process described in Example 16 was followed for preparing other 1-(4-aminophenyl)-3-R-4-methyl-7,8 -methylene-dioxy-3,4-dihydro-5H-2,3-benzodiazepines of the general Formula (I). The data of the products prepared are presented in Table 9.

TABLE 9

Products of the general formula (I) wherein $R_2 = CH_3$ and $R_1 = R_3 = R_4 = H$

| Example No. | R | M.p. °C. |
| --- | --- | --- |
| 17 | Trifluoroacetyl | 215–217 |
| 18 | Propionyl | 211–213 |
| 19 | Valeryl | 178–180 |
| 20 | Pivaloyl | 233–235 (d) |
| 21 | Benzoyl | 220–222 |
| 22 | Phenylacetyl | 220–221 |
| 23 | Cyclopropylcarbonyl | 138–140 |
| 24 | Cyanoacetyl | 123–126 |
| 25 | Methoxyacetyl | 125–127 |

(d) = decomposition

The new nitro compounds of the general formula (V), wherein R=H or acyl group, used in the preparation of products of Examples 16 to 25, can be prepared by processes described in Examples 26 to 36.

Example 26

1-(4-Nitrophenyl)-4-methyl-7,8-methylenedioxy-3,4-dihydro-5H-2,3-benzodiazepine To a suspension of 5.0 g (15.5 mmol) of the known 1-(4 -nitrophenyl)-4-methyl-7,8-methylenedioxy-5H-2,3-benzodiazepine (French patent specification No. 85,09793) in 380 ml of ethanol first 22.5 ml (0.278 mol) of concentrated hydrochloric acid were added at constant stirring whereupon a solution was formed within a few minutes, then 11.5 g (0.3 mole) of sodium borohydride were charged into the solution portionwise during 30 minutes. Stirring was continued for 15 minutes, then the orange-coloured precipitate formed was filtered and extracted on the filter with 4×30 ml of chloroform. The combined chloroform filtrate was evaporated under reduced pressure, the crystalline residue was brought to a filter with 200 ml of distilled water, then washed with 3×20 ml of distilled water and dried at 80°–100° C. to yield 4.90 g (97.2%) of the aimed product, m.p.: 162°–164° C. $C_{17}H_{15}N_3O_4=325.331$

EXAMPLE 27

1-(4-Nitrophenyl)-3-acetyl-4-methyl-7,8-methylenedioxy-3,4-dihydro-5H-2,3-benzodiazepine A 2.0 g (6.15 mmol) portion of the product of Example 26 was stirred with 10 ml of acetic anhydride at 25° C. for 3 hours then 50 ml of distilled water were added and the stirring was continued for one hour. The yellow precipitate formed was filtered, washed with 3×10 ml of distilled water and dried at 80°–100° C. to obtain 2.6 g of raw product. After recrystallization from 10 ml of ethanol 1.94 g (85.8%) of the aimed product were obtained, m.p.: 140°–142° C. $C_{19}H_{17}N_3O_5=367.369$

EXAMPLE 28

1-(4-Nitrophenyl)-3-trifluoroacetyl-4-methyl-7,8-methylenedioxy-3,4-dihydro-5H-2,3-benzodiazepine To a solution of a 1.5 g (4.61 mmol) portion of the product of Example 26 in 30 ml of anhydrous dichloromethane 0.75 ml (5.3 mmol) of trifluoroacetic acid anhydride and 0.75 ml (5.3 mmol) of triethylamine were added and the reaction mixture was stirred at 25° C. for 3 hours. Subsequently, the mixture was extracted with 3×20 ml of water and the organic layer was dried and evaporated under reduced pressure. The crystalline residue was treated with 15 ml of hot ethanol, cooled, filtered, washed with 3×1 ml of ethanol and dried at 80°–100° C. to yield 1.84 g (94.85%) of the aimed compound as a bright yellow crystalline product, m.p.: 165°–167° C. (decomp.). $C_{19}H_{14}F_3N_3O_5=421.339$

EXAMPLE 29

1-(4-Nitrophenyl)-3-propionyl-4-methyl-7,8-methylene-dioxy-3,4-dihydro-5H-2,3-benzodiazepine A 1.54 g (4.7 mmol) portion of the product of Example 26 was stirred with 8 ml of propionic acid anhydride at 25° C. for 3 hours, then 30 ml of diethyl ether were added and the solution was kept at 0°–5 ° C. overnight. The precipitate formed was filtered, washed with 3×8 ml of diethyl ether and dried to yield 1.32 g (73.7%) of the aimed compound as a light yellow product, m.p.: 189°–190° C. $C_{20}H_{19}N_3O_5=381.396$

EXAMPLE 30

1-(4-Nitrophenyl)-3-valeryl-4-methyl-7,8-methylene-dioxy-3,4-dihydro-5H-2,3-benzodiazepine To a solution of a.2.5. g (7.68 mmol) portion of the product of Example 26 in 40 ml of anhydrous dichloromethane 4.75 g (23 mmol) of dicyclohexylcarbodiimide and 2.88 g (23 mmol) of n-valeric acid were added and the reaction mixture was maintained at 25° C. under intermittent stirring for 24 hours. Then the N,N'-dicyclohexylurea formed as by-product was filtered, the filtrate was evaporated under reduced pressure, the residue was mixed with 2×40 ml of distilled water, decanted and the wet product was left to solidify under 50 ml of 50% ethanol. The solid compound was filtered, washed with 2×10 ml of 50% ethanol and dried at 80° C. The raw product obtained was recrystallized from 24 ml of ethanol and the crystals were dried at 100° C. to yield 2.20 g (70%) of the aimed product as a yellow powder, m.p.: 145°–147° C.
$C_{22}H_{23}N_3O_5=409.450$

EXAMPLE 31

1-(4-Nitrophenyl)-3-pivaloyl-4-methyl-7,8-methylene-dioxy-3,4-dihydro-5H-2,3-benzodiazepine By following the process described in Example 28 but applying pivaloyl chloride insted of trifluoroacetic acid anhydride, 1.68 g (89.4%) of the aimed product were obtained, m.p.: 164°–166° C.
$C_{22}H_{23}N_3O_5=409.450$

EXAMPLE 32

1-(4-Nitrophenyl)-3-benzoyl-4-methyl-7,8-methylene-dioxy-3,4-dihydro-5H-2,3-benzodiazepine By following the process described in Example 31 but using benzoyl chloride as acyl chloride, 1.72 g (86.9%) of an ochre yellow product were obtained, m.p.: 222°–224° C. (decomp.).
$C_{24}H_{19}N_3O_5=429.440$

EXAMPLE 33

1-(4-Nitrophenyl)-3-phenylacetyl-4-methyl-7,8-methylenedioxy-3,4-dihydro-5H-2,3-benzodiazepine By following the process described in Example 30 but using 50% of the calculated molar amount of dicyclohexylcarbodiimide and phenylacetic acid, a bright yellow product was obtained, m.p.: 193°–195° C.
$C_{25}H_{21}N_3O_5=443.467$

EXAMPLES 34 to 36

The products of Examples 34 to 36 were obtained by following the process described in Examle 33 and using the respective acid components.

EXAMPLE 34

1-(4-Nitrophenyl)-3-cyclopropanecarbonyl-4-methyl-7,8-methylenedioxy-3,4-dihydro-5H-2,3-benzodiazepine M.p.: 225°–228° C. (decomp.).
$C_{21}H_{19}N_3O_5=393.407$

EXAMPLE 35

1-(4-Nitrophenyl)-3-cyanoacetyl-4-methyl-7,8-methylene-dioxy-3,4-dihydro-5H-2,3-benzodiazepine M.p.: 185°–188° C.
$C_{20}H_{16}N_4O_5=392.380$

EXAMPLE 36

1-(4-Nitrophenyl)-3-methoxyacetyl-4-methyl-7,8-methylenedioxy-3,4-dihydro-5H-2,3-benzodiazepine M.p.: 187°–189° C.
$C_{20}H_{19}N_3O_6=397.396$

EXAMPLE 37

1-(4-Nitrophenyl)-3-(4-carboxybutyryl)-4-methyl-7,8-methylenedioxy-3,4-dihydro-5H-2,3-benzodiazepine By using the product of Example 26 as starting material and performing the acylation according to Example 14 with glutaric acid anhydride, finally recrystallizing the raw product from ethanol the pure aimed product was obtained, m.p.: 148°–150° C.
$C_{22}H_{21}N_3O_7=439.434$

EXAMPLE 38

1-(4-Aminophenyl)-3-phenylcarbamoyl-4-methyl-7,8-methylenedioxy-3,4-dihydro-5H-2,3-benzodiazepine To a solution of 0.70 g (2.3 mmol) of 1-(4-aminophenyl)-4-methyl-7,8-methylenedioxy-3,4-dihydro-5H-2,3 -benzodiazepine in 10 ml of anhydrous benzene 0.24 ml (2.3 mmol) of phenyl isocyanate was added and the reaction mixture was refluxed for one hour. Thereafter the solution was evaporated under reduced pressure and the amorphous residue was mixed with 20 ml of hot 50% ethanol. The suspension was cooled to 0° C. and filtered to yield 0.76 g of a raw product, m.p. 190°–200° C. After recrystallization from 99.5% ethanol and trituration with ethyl acetate the aimed compound melts at 207°–209° C.
$C_{24}H_{22}N_4O_3=414.472$ The preparation of the starting material of this example was described in the Hungarian patent specification No. 198,494. However, the compound may also be prepared by a new method according to the process of Example 16, by using the compound of Example 26 as starting material to give excellent yields (84%). The raw product may be recrystallized from 50% ethanol, m.p.: 118°–120° C.

EXAMPLE 39

1-(4-Diacetylaminophenyl)-3-acetyl-4-methyl-7,8-methylenedioxy-3,4-dihydro-5H-2,3-benzodiazepine 2.0 g (6.7 mmol) of 1-(4-aminophenyl)-4-methyl-7,8 -methylenedioxy-3,4-dihydro-5H-2,3-benzodiazepine were refluxed with 40 ml of acetic anhydride for 3 hours, then it was evaporated to dryness under reduced pressure. The crystalline residue was transferred with 25 ml of water to a filter and washed with 5×3 ml of water. After drying 2.79 g of the raw triacetyl derivative were obtained. After washing with 20 ml of isopropanol and drying at 100° C. 2.39 g (84.6 %) of the pure aimed product were obtained, m.p. 224°–227° C.
$C_{23}H_{23}N_3O_5=421.461$

EXAMPLE 40

N$^1$-[4-(3-Acetyl-4-methyl-7,8-methylenedioxy-3,4-dihydro-5H-2,3-benzodiazepin-1-yl)-phenyl]-N$^3$-methylurea 0.70 g (2 mmol) of the product of Example 15 was dissolved in benzene dehydrated over calcium hydride, 0.3 ml (5 mmol) of methyl isocyanate was added and the reaction mixture was stirred at 50° C. for 4 hours. The crystals formed after coling were filtered, washed with 3×3 ml of benzene, then triturated with 20 ml of hot benzene. The hot mixture was filtered, the precipitate was washed with 3×3 ml of benzene and dried to give 0.65 g (7.9.6%) of the aimed product, m.p.: 168°–170° C. (decomp.).
$C_{21}H_{22}N_4O_4$=394.439

EXAMPLE 41

N$^1$-[4-(3-Acetyl-4-methyl-7,8-methylenedioxy-3,4-dihydro-5H-2,3-benzodiazepin-1-yl)-phenyl]-N$^3$-phenylurea By following the process described in Example 40 but using phenyl isocyanate instead of methyl isocyanate, refluxing the reaction mixture for 10 hours, evaporating it under reduced pressure, then suspending the residue first in 50 ml of diethyl ether and then in 15 ml of ethyl acetate, 0.69 g (75.7%) of the aimed product was obtained, m.p.: 184°–186° C. (decomp.).
$C_{26}H_{24}N_4O_4$=456.510

EXAMPLE 42

1-(4-Acetylaminophenyl)-3-acetyl-4-methyl-7,8-methylenedioxy-3,4-dihydro-5H-2,3-benzodiazepine 1.3 g (4.4 mmol) of 1-(4-aminophenyl)-3-acetyl-4-methyl-7,8-methylenedioxy-3,4-dihydro-5H-2,3-benzodiazepine were stirred at 20°–25° C. with 5 ml of acetic anhydride for one hour, then the yellow solution was poured into 100 g of ice-water and stirred until the decomposition of the excess anhydride became complete. The precipitate formed was filtered, washed with 3×10 ml of distilled water and dried to give 1.6 g of raw product. After recrystallization from 20 ml of benzene 1.50 g (89.85%) of the aimed product were obtained, m.p.: 158°–160° C. (decomp.).
$C_{21}H_{21}N_3O_4$=379.423

EXAMPLE 43

1-(4-Formylaminophenyl)-3-formyl-4-methyl-7,8-methylenedioxy-3,4-dihydro-5H-2,3-benzodiazepine To 6.0 ml (0.104 mol) of acetic anhydride 3.0 ml (0.08 mol) of 100 % formic acid were added dropwise at 0° C. during 5 minutes while constant stirring. The stirring was continued at 50° C. for 15 minutes. Thereafter 1 g (3.3 mmol) of 1-(4 -aminophenyl)-4-methyl-7,8-methylenedioxy-3,4-dihydro-5H-2,3 benzodiazepine was added to the thus-prepared mixed anhydride. The reaction mixture was stirred at 25° C. for 1.5 hours, then poured into ice-water, the precipitate formed was filtered, washed with 4×5 ml of distilled water and dried at 80° C. to give 0.80 g of raw product. After crystallization from 3 ml of ethyl acetate 0.65 g (56.2%) of the aimed product was obtained, m.p.: 193°–195° C.
$C_{19}H_{17}N_3O_4$=351.369

EXAMPLE 44

1-(4-Trifluoroacetylaminophenyl)-3-trifluoroacetyl-4-methyl-7,8-methylenedioxy-3,4-dihydro-5H-2,3-benzodiazepine 1.48 g (5 mmol) of 1-(4-aminophenyl)-4-methyl-7,8 -methylenedioxy-3,4-dihydro-5H-2,3-benzodiazepine were dissolved in 30 ml of anhydrous chloroform, then 2.1 ml (15 mmol) of triethylamine and at 20°–25° C. 2.12 ml (15 mmol) of trifluoroacetic anhydride were added and the reaction mixture was stirred for 2.5 hours, then extracted first with 2×30 ml of water and thereafter with 20 ml of 5% hydrochloric acid. The organic layer was dried over anhydrous sodium sulfate, evaporated under reduced pressure and the amorphous residue was recrystallized from 10 ml of 70% ethanol to give 1.41 g (57.9%) of the aimed diacyl derivative, m.p. 177°–178° C.
$C_{21}H_{15}F_6N_3O_4$=487.363

EXAMPLE 45

1-(4-Propionylaminophenyl)-3-propionyl-4-methyl-7,8-methylenedioxy-3,4-dihydro-5H-2,3-benzodiazepine The process described in Example 44 was followed, except that 11.2 mmol of both triethylamine and propionic acid anhydride were used and the crystalline residue was recrystallized first from 15 ml of 50% ethanol, then from 11.5 ml of 99% ethanol to give 2.48 g (60.9%) of the aimed product, m.p.: 152°–154° C.
$C_{23}H_{25}N_3O_4$=407.477

EXAMPLES 46 to 65

Other diacyl derivatives of the general formula (I), wherein R=acyl group, R$^1$=R$^3$=H, R$^2$=CH$_3$ and R$^4$=acyl group, where R and R$^4$ are the same or different, are presented in Table 10. These compounds were prepared partly from compounds of the general formula (III), wherein R=R$^1$=R$^3$=H and R$^4$=acyl group; and partly from new compounds of the general formula (I), wherein R=acyl group, R$^1$=R$^3$=R$^4$=H and R$^2$=CH$_3$, according to processes defined in the preceding examples.

The preparation of starting substances of general formula (III), wherein R=R$^1$=R$^3$=H and R$^4$=acyl group is illustrated in detail below on the derivative bearing acetyl group as R$^4$:

1-(4-Acetylaminophenyl)-4-methyl-7,8-methylenedioxy-3,4-dihydro-5H-2,3-benzodiazepine

Method A

To a solution containing 6.0 g (20 mmol) 1-(4-aminophenyl)- 4-methyl-7,8-methylenedioxy-3,4-dihydro-5H-2,3 -benzodiazepine in 30 ml of ethyl acetate 1.38 ml (21 mmol) of methanesulfonic acid were added. The crystalline precipitate was filtered and washed with 5×5 ml of ethyl acetate. The dry weight of the product was 7.37 g, m.p.: it sintered above 190° C. and weakly decomposed at 210°–212° C. The thus-obtained methanesulfonate salt of the starting substance was acetylated as follows:

7.37 g of the powdered salt were suspended in 110 ml of acetic anhydride, the suspension was stirred at room temperature for 2 hours, then the crystalline precipitate was filtered, washed with 5×10 ml of ethyl acetate and dried to give 6.54 g of methanesulfonate salt of the target compound, m.p. 240°–241° C. (with decomposition).

The base was liberated from the methanesulfonate salt of the target compound e.g. in the following way: 6.54 g of salt were dissolved in 90 ml of water, the solution was clarified by charcoal, then 3.6 g of sodium hydrogen carbonate were portionwise added to the clear solution. The precipitate was filtered, washed with 5×10 ml of water and dried to obtain 5.54 g of crude product. After recrystallization from 130 ml of isopropanol, 3.11 g (yield 46%) of product were obtained, m.p.: 221°–223° C. (weak decomposition), the melting point Physical characteristics of other 1-(4-acylamino-phenyl)-4-methyl-7,8-methylenedioxy-3,4-dihydro-5H-2,3 -benzodiazepine are as follows:

| $R^4$-Analoque | M.p. °C. |
|---|---|
| Propionyl | 237–239 |
| Benzoyl | 247–248 (decomp.) |
| Phenylacetyl | 213–215 (decomp.) |
| Pivaloyl | 132–135 (decomp.) |

TABLE 10

Compounds of the general formula (I), wherein $R^1 = R^3 = H$, $R^2 = CH_3$, R and $R^4$ are acyl groups

| Example No. | R | $R^4$ | Starting material Example No. | Process of Example No. | M.p. °C. |
|---|---|---|---|---|---|
| 46 | $COCH_3$ | CHO | 15 (16) | 2, 30 | 142–144 |
| 47 | $COCF_3$ | $COCH_3$ | (III), $R^4 = COCH_3$ | 28, 44 | 212–214 |
| 48 | $COCH_3$ | $COC_2H_5$ | 15 (16) | 28, 44 | 155–157 |
| 49 | $COC_2H_5$ | $COCH_3$ | (III), $R^4 = COCH_3$ | 28, 44 | 168–170 |
| 50 | $COCH_3$ | $CO-C(CH_3)_3$ | 15 (16) | 31 | 201–203 |
| 51 | $CO-C(CH_3)_3$ | $COCH_3$ | (III), $R^4 = COCH_3$ | 31 | 138–140 |
| 52 | $COCH_3$ | $CO-CH_2-OCH_3$ | 15 (16) | 2, 30 | 118–120 |
| 53 | $CO-CH_2-OCH_3$ | $COCH_3$ | (III), $R^4 = COCH_3$ | 2, 30 | 136–138 (d) |
| 54 | $COCH_3$ | $CO-CH_2-CN$ | 15 (16) | 2, 30 | 149–151 (d) |
| 55 | $CO-CH_2-CN$ | $COCH_3$ | (III), $R^4 = COCH_3$ | 2, 30 | 128–130 (d) |
| 56 | $CO-C_6H_5$ | $COCH_3$ | (III), $R^4 = COCH_3$ | 31 | 154–156 |
| 57 | $COCH_3$ | $CO-C_6H_5$ | 15 (16) | 31 | 214–216 |
| 58 | $CO-(CH_2)_3-COOH$ | $COCH_3$ | (III), $R^4 = COCH_3$ | 14 | 172–174 |
| 59 | $COCH_3$ | $CO-(CH_2)_3-COOH$ | 15 (16) | 14 | 210–212 (d) |
| 60 | CHO | $COC_2H_5$ | (III), $R^4 = COC_2H_5$ | 2 | 185–187 |
| 61 | CHO | $CO-C(CH_3)_3$ | (III), $R^4 = CO-C(CH_3)_3$ | 2 | 220–221 (d) |
| 62 | $COCH_3$ | $COCF_3$ | 15 (16) | 28 | 150–152 (d) |
| 63 | CHO | $CO-C_6H_5$ | (III), $R^4 = CO-C_6H_5$ | 2 | 202–203 (d) |
| 64 | $COCH_3$ | $CO-CH_2-C_6H_5$ | (III), $R^4 = CO-CH_2-C_6H_5$ | 2 | 135–137 |
| 65 | $COC_2H_5$ | CHO | 18 | 2 | 140–141 (d) |

(d) = decomposition of which increased to 223°–225° C. after digesting with 15 ml of hot benzene.
$C_{19}H_{19}N_3O_3$=337.385
The hydrochloride salt decomposed at 262°–264° C.

Method B

After dissolving 15.0 g (44.7 mmol) of 1-(4-acetylaminophenyl)- 4-methyl-7,8-methylenedioxy-5H-2,3-benzodiazepine in 150 ml of pyridine under mild heating, 10.2 g (0.269 mol) of sodium borohydride were added and the mixture was stirred on an oil bath at a temperature of 100° C. for 5 hours. Then the reaction mixture was cooled to about 25° C., 150 ml of water were dropwise added under continuous stirring during 20 minutes, thereafter a mixture containing 180 ml of concentrated hydrochloric acid and 265 ml of water was added while cooling with ice-water. A yellowish suspension was formed. The precipitate was filtered, washed with 5×20 ml of water and dried to yield 15.2 g of salt, m.p. above 250 ° C. In order to liberate the base, this salt was suspended in 150 ml of 50% ethanol and then 5.7 g of sodium hydrogen carbonate were portionwise added while stirring. The thus-formed suspension was filtered after 30 minutes, washed successively with 3×10 ml of 50% ethanol, 5×20 ml of water, finally with 20 ml of 50% ethanol and dried to obtain 10.95 g of a crude product, m.p.: 218°–220° C. (weak decomposition). After digesting this crude product with 50 ml of hot isopropanol and then with 100 ml of hot 99.5% ethanol, 8.63 g (57.2%) of the aimed compound were obtained, m.p.: 220°–222° C. (weak decomposition).

EXAMPLE 66

1-(4-Glycylaminophenyl)-4-methyl-7,8-methylenedioxy-5H-2,3-benzodiazepine

To a suspension of 2.89 g (5.97 mmol) of 1-(4 -phthaloylglycylaminophenyl)-4-methyl-7,8-methylenedioxy-5 H-2,3-benzodiazepine (Example 79) in 50 ml of methanol 0.6 ml (11.9 mmol) of 100% hydrazine hydrate was added and the mixture was refluxed for 2 hours. The reaction mixture was cooled, evaporated under reduced pressure, the partially crystalline residue was mixed with 40 ml of dichloromethane, filtered and the by-product was washed with 2×10 ml of dichloromethane. The solution was extracted with 3×15 ml of 5 hydrochloric acid, the aqueous layer was made alkaline with 24 ml of aqueous 10% sodium hydroxide, the precipitate formed was filtered, washed with 3×10 ml of distilled water and dried at 100° C. to obtain 1.67 g of raw product. After recrystallization from 73 ml of ethanol 1.50 g (71.8%) of the aimed product were obtained, m.p.: 223°–225° C.

$C_{19}H_{18}N_4O_3$=350,385

EXAMPLES 67 to 78

Other compounds of the general formula (I), wherein $R^2=CH_3$, $R^3=H$, and some of their acid addition salts, prepared by the process of Example 66, are presented in Table 11. The salts were prepared by known methods.

TABLE 11

| Example No. | R | R¹ | R⁴ | Example No. of starting material | M.p. °C. (salt) |
|---|---|---|---|---|---|
| 67 | — | — | CO—(CH$_2$)$_3$—NH$_2$ | 80 | 198–200 (d) |
| 68 | — | — | DL—CO—CH(CH$_3$)—NH$_2$ | 81 | 155–157 (d) |
| 69 | — | — | DL—CO—CH(CH$_3$)—NH$_2$ | 68 | 217–219 (d) (H—Fu) |
| 70 | CO—CH$_2$—NH$_2$ | H | H | 82 | 150–155 |
| 71 | CO—CH$_2$—NH$_2$ | H | H | 70 | 190–193 (d) (H—Fu) |
| 72 | DL—CO—CH(CH$_3$)—NH$_2$ | H | H | 84 | 193–195 [H—Fu 210–213 (d)] |
| 73 | COCH$_3$ | H | CO—CH$_2$—NH$_2$ | 88 | 210–211 (d) (HCl) [base 230–232 (d)] |
| 74 | CO—CH$_2$—CH$_2$ | H | COCH$_3$ | 89 | 210–212 (d) |
| 75 | CO—(CH$_2$)$_3$—NH$_2$ | H | COCH$_3$ | 90 | 154–156 (d) (Fu) |
| 76 | (H—Fu), COCH$_3$ | H | DL—CO—CH(CH$_3$)—NH$_2$ | 91 | 222–223 (d) (H—Fu) |
| 77 | DL—CO—CH(CH$_3$)—NH$_2$ | H | COCH$_3$ | 92 | 218–220 (d) |
| 78 | CO—CH$_2$—NH$_2$ | H | CO—CH$_2$—NH$_2$ | 93 | 202–204 (d) |

Notes:
H—Fu = hydrogen fumarate (H-fumarate), Fu = fumarate
The products of Examples 70 to 72 were prepared from the corresponding starting substances in two steps, by following first Example 66 and then Example 16.

EXAMPLE 79

1-[4-(N-Phthaloylglycylamino)phenyl]-4-methyl-7,8-methylenedioxy-5H-2,3-benzodiazepine To a solution of 2.0 g (6.88 mmol) of 1-(4-amino-phenyl)-4-methyl-7,8-methylenedioxy-5H-2,3-benzodiazepine in dichloromethane 1.84 g (8.94 mmol) of dicyclohexylcarbodiimide and 1.84 g (8.94 mmol) of powdered phthalimidoacetic acid were added and the reaction mixture was stirred at 25° C. for 8 hours, then left to stand at 0°–5° C. overnight. The precipitate formed was filtered, washed with 3×3 ml of dichloromethane and dried at 60°–80° C. to result in 5 g of a product consisting of a mixture of the target product and N,N'-dicyclohexylurea, a by-product. This mixture was purified by refluxing with 210 ml of ethanol for 30 minutes, filtering the hot mixture and washing with 2×10 ml of hot ethanol, thereafter drying at 100° C. to obtain 2.42 g (73.3 of the aimed product, m.p.: 266°–268° C. (decomp.). C$_{27}$H$_{20}$N$_4$O$_5$=480.489

EXAMPLE 80

1-[4-(N-Phthaloyl-γ-aminobutyrylamino)phenyl]-4-methyl-7,8-methylenedioxy-5H-2,3-benzodiazepine By following the process described in Example 79 but using -phthalimidobutyric acid, 3.8 g of a mixture were obtained, which was combined with the dichloromethane mother liquor extracted previously with 2×40 ml of a 10% aqueous sodium carbonate solution. After evaporating under reduced pressure the residue was submitted to column chromatography [adsorbent: Kieselgel 60 (0.063–2 mm), eluent: ethyl acetate-methanol 4:1]. The evaporation residue was triturated with 10 ml of hot ethanol, cooled, filtered, washed with 3×1 ml of ethanol and dried to give 3.12 g (90%) of the aimed product, m.p.: 233°–235° C. (decomp.). C$_{29}$H$_{24}$N$_4$O$_5$=508.543

EXAMPLE 81

1-[4-(N-Phthaloyl-DL-alanylamino)phenyl]-4-methyl-7,8-methylenedioxy-5H-2,3-benzodiazepine The process described in Example 79 was followed, except that N-phthaloyl-DL-alanine (DL-2-phthalimidopropionic acid) was used. After filtering the slight precipitate formed the filtrate was evaporated, the residue was mixed with 15 ml of dichloromethane, carefully filtered and the clear solution obtained was repeatedly evaporated. The purification of the residue was achieved by refluxing it with 60 ml of ethyl acetate. Crystal formation was already started in the hot solution. The crystals were filtered at 0°–5° C., the nearly white crystal powder was washed with 3×3 ml of ethyl acetate and dried at 100° C. to give 2.75 g (80.95%) of the aimed product, m.p.: 243°–245° C. (decomp.). C$_{28}$H$_{22}$N$_4$O$_5$=494.516

EXAMPLE 82

1-(4-Nitrophenyl)-3-glycyl-4-methyl-7,8-methylenedioxy-3,4-dihydro-5H-2,3-benzodiazepine The process described in Example 66 was followed by using the compound prepared according to Example 85 as starting material, but the dichloromethane solution was extracted only with 3×20 ml of distilled water and the organic layer was evaporated under reduced pressure. The crystalline residue was purified by suspending it in 7 ml of ethanol to give the pure aimed product in a yield of 86.1%, m.p.: 201°–203° C. (decomp.). C$_{19}$H$_{18}$N$_4$O$_5$=382.385

EXAMPLE 83

1-(4-Nitrophenyl)-3-(γ-aminobutyryl)-4-methyl-7,8-methylenedioxy-3,4-dihydro-5H-2,3-benzodiazepine By following the process described in Example 82 and using the compound prepared according to Example 86 as starting material, a product containing crystal solvent was obtained in a yield of 89.4%, m.p. 110°–112° C. (recrystallized from 50% ethanol).
C$_{21}$H$_{22}$N$_4$O$_5$=410.439

EXAMPLE 84

1-(4-Nitrophenyl)-3-(DL-alanyl)-4-methyl-7,8-methylenedioxy-3,4-dihydro-5H-2,3-benzodiazepine By following the process described in Example 82 and using the compound pepared according to Example 87 the aimed compound was obtained, m.p. 220°–221° C. (decomp.).
C$_{20}$H$_{20}$N$_4$O$_5$=396.412

EXAMPLES 85 to 87

The new intermediates employed in Examples 82 to 84 as starting materials were prepared from the compound prepared according to Example 26 by the process of Example 81.

EXAMPLE 85

1-(4-Nitrophenyl)-3-(N-phthaloylglycyl)-4-methyl-7,8-methylenedioxy-3,4-dihydro-5H-2,3-benzodiazepine Yield: 93.3%, m.p.: 173°–174° C. (decomp.).
$C_{27}H_{20}N_4O_7=512.489$

EXAMPLE 86

1-(4-Nitrophenyl)-3-(N-phthaloyl-γ-aminobutyryl)-4-methyl-7,8-methylenedioxy-3,4-dihydro-5H-2,3-benzodiazepine M.p.: 218°–220° C.
$C_{29}H_{24}N_4O_7=540.543$

EXAMPLE 87

1-(4-Nitrophenyl)-3-(N-phthaloyl-DL-alanyl)-4-methyl-7,8-methylenedioxy-3,4-dihydro-5H-2,3-benzodiazepine M.p.: 210°–212° C.
$C_{28}H_{22}N_4O_7=526.516$

EXAMPLE 88 to 94

The intermediates of the general formula (I), wherein R and/or R4 represent(s) $C_{1-6}$ acyl group(s) substituted by a phthalimido group, are required for the preparation of compounds obtained by using the processes of Examples 73 to 78 and summarized in Table 12. They were prepared from the compound of Example 15 (16) or from a compound of the general formula (III), wherein $R_4$ is hydrogen (see U.S. Pat. No. 4,835,152) or from 1-(4-acetylaminophenyl)-4-methyl-7,8-methylenedioxy-3,4-dihydro-5H-2,3-benzodiazepine described hereinabove (before Table 10) by following the process of Example 81.

As a matter of course, in Example 93 a twofold amount of phthaloylglycine and dicyclohexylcarbodiimide have to be used. Thus, Table 12 lists new compounds of the general formula (I), wherein R and $R^4$ are acyl groups, $R^1=R^3=H$ and $R^2=CH_3$.

EXAMPLE 95

1-(4-Aminophenyl)-3-(γ-aminobutyryl)-4-methyl-7,8-methylenedioxy-3,4-dihydro-5H-2,3-benzodiazepine hydrogen fumarate It was prepared from the compound of Example 83 by following Example 16, m.p.: 150°–152° C. (decomp.)
$[C_{29}H_{25}N_4O_3].C_4H_3O_4=496.531$

EXAMPLE 96

1-(4-Aminophenyl)-3-(4-carboxybutyryl)-4-methyl-7,8-methylenedioxy-3,4-dihydro-5H-2,3-benzodiazepine hydrochloride It was obtained from the compound of Example 37, according to Example 16, m.p.: 224°–226° C. (decomp.).
$[C_{22}H_{24}N_3O_5]Cl=445.915$

EXAMPLE 97

1-(4-Trifluoroacetylaminophenyl)-4-methyl-7,8-methylenedioxy-5H-2,3-benzodiazepine It was prepared by following Example 2, m.p.: 258°–260° C. (decomp.).
$C_{19}H_{14}F_3N_3O_3=389.339$

EXAMPLE 98

1-(4-Aminophenyl)-3-methylcarbamoyl-4-methyl-7,8-methylenedioxy-3,4-dihydro-5H-2,3-benzodiazepine It was prepared from 1-(4-nitrophenyl)-3-methyl-carbamoyl-4-methyl-7,8-methylenedioxy-3,4-dihydro-5H-2,3-benzodiazepine according to Example 16, m.p. 199°–201° C.
$C_{19}H_{20}N_4O_3=352.401$
Hydrochloride m.p. 219°–221° C. (decomp.).
$C_{19}H_{21}N_4O_3]Cl=388.866$ The starting nitro compound was prepared as follows:
1.1 ml (18.4 mmol) of methyl isocyanate were added to 3.0 g (9.22 mmol) of 1-(4-nitrophenyl)-4-methyl-7,8-methylene-dioxy-3,4-dihydro-5H-2,3-benzodiazepine (see Example 26) dissolved in 60 ml of dichloromethane and stirred for 24 hours; then evaporated under reduced pressure. The crystalline residue was triturated with 30 ml of hot ethanol at 80° to 100° C. to obtain 3.35 g (95%) of the lemon-yellow aimed product, m.p.: 238°–240° C. (decomp.).
$C_{19}H_{18}N_4O_5=382.385$

TABLE 12

| Example No. | R | $R^4$ | M.p. °C. |
|---|---|---|---|
| 88 | $COCH_3$ | $CO-CH_2-N(CO)_2C_6H_4$ | 314–316 (d) |
| 89 | $CO-CH_2-N(CO)_2C_6H_4$ | $COCH_3$ | 204–206 (d) |
| 90 | $CO-(CH_2)_3-N(CO)_2C_6H_4$ | $COCH_3$ | 150–152 |
| 91 | $COCH_3$ | $DL-CO-CH(CH_3)-N(CO)_2C_6H_4$ | 264–266 (d) |
| 92 | $DL-CO-CH(CH_3)-N(CO)_2C_6H_4$ | $COCH_3$ | 245–248 |
| 93 | $CO-CH_2-N(CO)_2C_6H_4$ | $CO-CH_2-N(CO)_2C_6H_4$ | 230–232 (d) |
| 94 | $COCH_3$ | $CO-(CH_2)_3-N(CO)_2C_6H_4$ | 173–175 |

$(CO)_2C_6H_4$ = phthaloyl; $N(CO)_2C_6H_4$ = phtalimido; (d) = decomposition

EXAMPLE 99

1-(4-Aminophenyl)-3-(1-pyrrolidinoacetyl)-4-methyl-7,8-methylenedioxy-3,4-dihydro-5H-2,3-benzodiazepine It was obtained from 1-(4-nitrophenyl)-3-(1-pyrrolidinoacetyl)-4-methyl-7,8-methylenedioxy-3,4-dihydro-5H- 2,3-benzodiazepine by following Example 16, m.p.: 212°–214° C.
$C_{23}H_{26}N_4O_3$=406.493

The starting substance was obtained from 1-(4-nitrophenyl)-3-chloroacetyl-4-methyl-7,8-methylenedioxy-3,4-dihydro-5H-2,3-benzodiazepine (see Example 116) according to Example 102, m.p.: 189°–190° C. (decomp.).
$C_{23}H_{24}N_4O_5$=436.477

EXAMPLE 100

1-(4-Aminophenyl)-3-(N,N-dimethylglycyl)-4-methyl-7,8-methylenedioxy-3,4-dihydro-5H-2,3-benzodiazepine hydrogen fumarate It was prepared fr4om 1-(4-nitrophenyl)-3 -(N,N-dimethylglycyl)-4-methyl-7,8-methylenedioxy-3,4-dihydro- 5H-2,3-benzodizapine according to Example 16, m.p.: 202°–204° C. (decomp.).
$C_{21}H_{25}N_4O_3]C_4H_3O_4$=496.531

The starting substance was obtained from 1-(4-nitrophenyl)- 3-chloroacetyl-4-methyl-7,8-methylenedioxy-3,4-dihydro-5H-2,3-benzodiazepine according to the process described in Example 103, m.p.: 158°–160° C.
$C_{21}H_{22}N_4O_5$=410.439

EXAMPLE 101

1-(4-Chloroacetylaminophenyl)-4-methyl-7,8-methylenedioxy-5H-2,3-benzodiazepine

It was prepared according to Example 2, except that chloroacetic acid was used, m.p.: 209°–214° C. (carbonization).
$C_{19}H_{16}ClN_3O_3$=369.818

EXAMPLE 102

1-[4-(1-Pyrrolidinoacetylamino)phenyl]-4-methyl-7,8-methylenedioxy-5H-2,3-benzodiazepine 0.71 ml (8.53 mmol) of pyrrolidine was added to a suspension of 1.5 g ( 406 mmol) of 1-(4-chloroacetylaminophenyl)- 4-methyl-7,8-methylenedioxy-5H-2,3-benzodiazepine in 60 ml of ethanol and the reaction mixture was refluxed for 4 hours, then evaporated under reduced pressure. The residue was treated with water to give a rough product (1.49 g), m.p.: 186°–188° C. After recrystallization from 12 ml of ethanol 1.22 g (74.4%) of the aimed product were obtained, m.p.: 210°–212° C.
$C_{23}H_{24}N_4O_3$=404 477

EXAMPLE 103

1-[4-(N,N-dimethylglycylamino)phenyl]-4-methyl-7,8-methylenedioxy-5H-2,3-benzodiazepine After adding 0.66 g (8.12 mmol) of dimethylamine hydrochloride and 1.86 ml (13.4 mmol) of triethylamine to a suspension of 1.5 g (4.06 mmol) of 1-(4-chloroacetylaminophenyl)- 4-methyl-7,8-methylenedioxy-5H-2,3-benzodiazepine in 60 ml of ethanol, the reaction mixture was refluxed for 8 hours, then evaporated. The residue was dissolved in 30 ml of dichloromethane, washed with 20 ml of 4% NaOH solution, then 2×20 ml of distilled water, dried and evaporated under reduced pressure. After treating with water, the crystalline residue was filtered to give 1.27 g of raw product, m.p. 211°–213° C. After recrystallization from 10 ml of ethanol 1.1 g (71.4%) of aimed product were obtained, m.p.: 213°–215° C.
$C_{21}H_{22}N_4O_6$=378.439

EXAMPLE 104

1-(4-Methylcarbamoylaminophenyl)-4-methyl-7,8-methylenedioxy-5H-2,3-benzodiazepine 0.8 ml (13.4mmol) of methyl isocyanate was added to a solution containing 1.0 g (3.41 mmol) of 1-(4-aminophenyl)-4 -methyl-7,8-methylenedioxy-5H-2,3-benzodiazepine in 8 ml of dimethylformamide (DMF), then the reaction mixture was stirred at 25° C. for 24 hours. After diluting with 80 ml of water, filtering at 5° C. and drying at 60° to 100° C., 1.06 g of raw product, m.p.: 204°–207° C. (sintering from 160° C.) were obtained which, when recrystallized from 5 ml of ethanol, gave 0.85 g (71.4%) of the aimed product, m.p.: 223°–224° C. (decomp.).
$C_{19}H_{18}N_4O_3$=350.385

EXAMPLE 105

1-(4-Acetylaminophenyl) -3-methylcarbamoyl-4-methyl-7,8-methylenedioxy-3,4-dihydro-5H-2,3-benzodiazepine It was prepared from 1-(4-aminophenyl)-3-methylcarbamoyl- 4-methyl-7,8-methylenedioxy-3,4-dihydro-5H-2,3-benzodiazepine by using the process of Example 42. The raw product was recrystallized from ethyl acetate to give 71.4% of the aimed product, m.p.: 150°–152° C.
$C_{21}H_{22}N_4O_4$=394.439

EXAMPLE 106

1-(4-Chloroacetylaminophenyl)-3-acetyl-4-methyl-7,8-methylenedioxy-3,4-dihydro-5H-2,3-benzodiazepine It was prepared from 1-(4-aminophenyl)-3-acetyl-4-methyl-7,8-methylenedioxy-3,4-dihydro-5H-2,3-benzodiazepine by using the process of Example 2, m.p.: 139°–140° C.
$C_{21}H_{20}ClN_3O_4$=413.972

EXAMPLE 107

1-[4-(N,N-dimethylglycylamino)phenyl]-3-acetyl-4-methyl-7,8-methylenedioxy-3,4-dihydro-5H-2,3-benzodiazepine It was prepared from the product of the preceding Example by using the process described in Examle 103, m.p.: 206°–208° C.
$C_{23}H_{26}N_4O_4$=422.493

EXAMPLE 108

1-[4-(N,N-diethylglycylamino)phenyl]-3-acetyl-4-methyl-7,8-methylenedioxy-3,4-dihydro-5H-2,3-benzodiazepine It was prepared from 1-(4-chloroacetylamincphenyl)-3-acetyl-4-methyl-7,8-methylenedioxy-3,4-dihydro-5H-2,3-benzodiazepine and diethylamine by using the process described in Example 102, m.p.: 175°–176° C.
$C_{25}H_{30}N_4O_4$=450. 547

EXAMPLE 109

1-[4-(1-Pyrrolidinoacetylamino)phenyl]-3-acetyl-4-methyl-7,8-methylenedioxy-3,4-dihydro-5H-2,3-benzodiazepine hydrogen fumarate It was prepared from 1-(4-chloroacetylaminophenyl)-3-acetyl-4-methyl-7,8-methylenedioxy-3,4-dihydro-5H-2,3-benzodiazepine by using the process of Example 2 and isolated in the form of hydrogen fumarate, m.p.: 181°–183° C. ( decomp.).
$C_{25}H_{29}N_4O_4]\cdot C_4H_3O_4$=564.607

EXAMPLE 110

1-(4-Acetylaminophenyl)-3-chloroacetyl-4-methyl-7,8-methylenedioxy-3,4-dihydro-5H-2,3-benzodiazepine It was prepared from the compound of general formula (III), wherein $R^4$=COCH$_3$, by using the process of Examle 2 and chloroacetic acd instead of formic acid, m.p. 138°–140° C.
$C_{21}H_{20}ClN_3O_4$=413.972

EXAMPLE 111

1-[4-(N,N-diethylglycylamino)phenyl]-4-methyl-7,8-methylenedioxy-5H-2,3-benzodiazepine It was prepared from 1-(4-chloroacetylaminophenyl)-4-methyl-7,8-methylenedioxy-5H-2,3-benzodiazepine by using the process of Example 102, except that diethylamine was used instead of pyrrolidine, m.p.: 157°–158° C.
$C_{23}H_{26}N_4O_3$=406.493

EXAMPLE 112

1-(4-Acetylaminophenyl)-3-cyclopropanecarbonyl-4-methyl-7,8-methylenedioxy-3,4-dihydro-5H-2,3-benzodiazepine It was prepared from 1-(4-aminophenyl)-3-cyclopropanecarbonyl- 4-methyl-7,8-methylenedioxy-3,4-dihydro-5H-2,3 -benzodiazepine by using the process of Example 42, m.p.: 242°–243° C.
$C_{23}H_{23}N_3O_4$=405.461

EXAMPLE 113

$N^1$-[4-(3-Methylcarbamoyl-4-methyl-7,8-methylenedioxy-3,4-dihydro-5H-2,3-benzodiazepin-1-yl)phenyl]-$N^3$-methylurea After adding 0.5 ml (8.5 mmol) of methyl isocyanate to 0.6 g (1.7 mmol) of 1-(4-aminophenyl)-3-methylcarbamoyl-4 -methyl-7,8-methylenedioxy-3,4-dihydro-5H-2,3-benzodiazepine (see Example 98) dissolved in 45 ml of anhydrous dichloromethane, the reaction mixture was stirred at 25° C. for 6 days. Then the crystalline precipitate was filtered, washed with 3×2 ml of dichloromethane and dried at 60° to 80° C. to obtain 0.55 g (79.7%) of the pure aimed product, m.p.: 181°–183° C.
$C_{21}H_{23}N_5O_4$=409.455

EXAMPLE 114

1-(4-Aminophenyl)-3-n-butylcarbamoyl-4-methyl-7,8-methylenedioxy-3,4-dihydro-5H-2,3-benzodiazepine It was prepared from 1-(4-nitrophenyl)-3-n-butyl-carbamoyl- 4-methyl-7,8-methylenedioxy-3,4-dihydro-5H-2,3 -benzodiazepine, m.p.: 173°–175° C.
$C_{22}H_{26}N_4O_3$=394.482

The starting substance was prepared as described for the starting substance of Example 98, except that n-butyl isocyanate was used instead of methyl isocyanate and the reaction mixture was stirred for 5 days at 25° C., m.p. 176°–178° C.
$C_{22}H_{24}N_4O_5$=424.466

EXAMPLE 115

1-(4-Glycylaminophenyl)-3-methylcarbamoyl-4-methyl-7,8-methylenedioxy-3,4-dihydro-5H-2,3-benzodiazepine It was prepared from 1-[4-(N-phthaloylglycylamino)-phenyl]-3-methylcarbamoyl-4-methyl-7,8-methylenedioxy-3,4-dihydro-5H-2,3-benzodiazepine by using the process of Example 66 as modified in Example 82, m.p.: 163°–165° C.
$C_{21}H_{23}N_5O_4$=409.455

The starting substance was prepared from 1-(4-aminophenyl)- 3-methylcarbamoyl-4-methyl-7,8-methylenedioxy-3,4 -dihydro-5H-2,3-benzodiazepine (see Example 98) according to Example 79, m.p. 270°–271° C. (decomp.).
$C_{29}H_{25}N_5O_6$=539.559

EXAMPLE 116

1-(4-Aminophenyl)-3-(N-methylglycyl)-4-methyl-7,8-methylenedioxy-3,4-dihydro-5H-2,3-benzodiazepine 1.03 g (15.3 mmol) of methylamine hydrocdhloride and 2.64 ml (18.3 mmol) of triethylamine were added to a suspension containing 1.23 g (3.06 mmol) of 1-(4-nitrophenyl)-3 -chloroacetyl-4-methyl-7,8-methylenedioxy-3,4-dihydro-5H-2,3 -benzodiazepine in 140 ml of ethanol and the reaction mixture was refluxed for 10 hours, then evaporated under reduced pressure. The residue was dissolved in 30 ml of chloroform, washed with 20 ml of 4% NaOH solution, then 2×20 ml of water, dried and evaporated under reduced pressure. The residue was reduced according to the process of Example 16 and the product obtained was purified by column chromatography (adsorbent: Kieselgel 60, eluent: methanol—benzene 4:1). The crude product obtained was triturated with 5 ml of ethyl acetate at 25° C. to obtain 0.60 g (53.6%) of the aimed product, m.p. 198°–200° C. (weak decomp.).
$C_{20}H_{22}N_4O_3$=366.428)

The starting compound was obtained from 1-(4-nitrophenyl)-4-methyl-7,8-methylenedioxy-3,4-dihydro-5H-2,3-benzodiazepine (see Examle 26) and chloroacetic acid by using the process of Example 33, m.p. 189°–191° C. (decomp.).
$C_{19}H_{16}ClN_3O_5$=401.818

EXAMPLE 117

1-[4-(N-methylglycylamino)phenyl]-3-acetyl-4-methyl-7,8-methylenedioxy-3,4-dihydro-5H-2,3-benzodiazepine 1.31 g (19.5 mmol) of methylamine hydrochloride and 2.24 ml (23.3 mmol) of triethylamine were added to a suspension containing 1.61 g (3.89 mmol) of 1-(4-chloroacetylamino-phenyl)- 3-acetyl-4-methyl-7,8-methylenedioxy-3,4-dihydro-5H- 2,3-benzodiazepine (see Example 106) in 100 ml of ethanol and the reaction mixture was refluxed for 10 hours, then evaporated under reduced pressure. The residue was purified by column chromatography (adsorbent: Kieselgel 60, eluent: chloroform—methanol 9:1). The crude product was triturated with 3 ml of 50% ethanol at 25° C. to give 0.61 g (38.6%) of the aimed product, m.p.: 220°–222° C. (weak decomp.).
$C_{22}H_{24}N_4O_4$=408.466

EXAMPLE 118

Preparation of pharmaceutical compositions

Tablets or divided tablets containing 25 mg of 1-(4-aminophenyl)-3-acetyl-4-methyl-7,8-methylenedioxy-3,4-dihydro-5H-2,3-benzodiazepine (compound of Examples 15 or 16) or 25 mg of 1-(4-acetylaminophenyl)-3-acetyl-4-methyl- 7,8-methylenedioxy-3,4-dihydro-5H-2,3-benzodiazepine (compound of Example 42) or 25 mg of 1-(4-aminophenyl)-3 -methylcarbamoyl-4-methyl-7,8-methylenedioxy-3,4-dihydro-5H- 2,3-benzodiazepine (compound of Example 98) each as active ingredient were prepared by usual methods.

| Active ingredient | 25 mg |
| --- | --- |
| Potato starch | 43 mg |
| Lactose | 160 mg |
| Polyvinylpyrrolidone | 6 mg |
| Magnesium stearate | 1 mg |
| Talc | 30 mg |
| b) An other preferred composition of one tablet: | |
| Active ingredient | 25 mg |
| Lactose | 130 mg |
| Maize starch | 25 mg |
| Microcrystalline cellulose | 10 mg |
| Gelatine | 4 mg |
| Talc | 2 mg |
| Stearin | 1 mg |
| Magnesium stearate | 1 mg |

EXAMPLE 119

(−)-1-(4-Nitrophenyl)-4-methyl-7,8-methylenedioxy-3,4-dihydro-5H-2,3-benzodiazepine A solution of (S)-(−)-2-amino-3-methyl-1,1 -diphenylbutan-1-ol (4.75 g) in dry methylene chloride was cooled to −70° C. and treated with a solution of borane in THF (1.8 M, 9.5 ml) over a 20 minute period under an atmosphere of dry nitrogen. The resulting solution was gradually warmed to 0° C. and allowed to stand overnight at 4° C. This mixture was treated with a solution of 1-(4 -nitrophenyl)-4-methyl-7,8-methylenedioxy-5H-2,3 -benzodiazepine (5.0 g) in dry methylene chloride (100 ml) at room temperature over a period of about 1 hour. The resulting solution was allowed to stand at room temperature for seven days. The reaction was quenched by the addition of 10% sodium carbonate (15 ml). The resulting phases were separated, and the organic layer washed with water (2×50 ml), dried over sodium sulfate, and concentrated in vacuo to give a yellow crystalline solid. This solid was suspended in ethanol (50 ml), filtered, and dried to give 4.47 g of the title compound. Proton NMR spectroscopy using a shift reagent (Eu(hfc)$_3$) shows the product as 90:10 mixture of enantiomers. This material was dissolved in hot ethyl acetate (24 ml) and allowed to stand at room temperature overnight.. The crystalline precipitate was separated by filtration, washed with ethyl acetate (3×5 ml), and dried to give 2.87 g of the title compound. Proton NMR spectroscopy using a shift reagent (Eu(hfc)$_3$) shows this material to have an enantiomeric purity of more than 98%. Melting point 171°–172.5° C.
$[\alpha]_D$=−155.6° (c=1, CHCl$_3$)

EXAMPLE 120

(+)-1-(4-Nitrophenyl)-4-methyl-7,8-methylenedioxy-3,4-dihydro-5H-2,3-benzodiazepine The title compound was prepared as described in Example 119 using (R)-(+)-2-amino-3-methyl-1,1 -diphenylbutan-1-ol. Melting point 172°–174° C.
$[\alpha]_D$=+153.40° (c=1, CHCl$_3$)
Enantiomeric purity: 98%

EXAMPLE 121

(−)-1-(4-Nitrophenyl)-3-methylcarbamoyl-4-methyl-7,8-methylenedioxy-3,4-dihydro-5H-2,3-benzodiazepine A solution of the compound prepared as described in Example 119 (4.0 g) in dry methylene chloride (80 ml) was treated with methylisocyanate (2.18 ml). The resulting reaction mixture was stirred at room temperature for three days. This reaction mixture was evaporated in vacuo and the oily residue treated with water (60 ml). The resulting precipitate was filtered and dried to give 4.49 g of the title compound was a yellow powder. This material was used in the next step without further purification.
$[\alpha]_D$=−315.3° (c=1, CHCl$_3$)

EXAMPLE 122

(+)-1-(4-Nitrophenyl)-3-methylcarbamoyl-4-methyl-7,8-methylenedioxy-3,4-dihydro-5H-2,3-benzodiazepine The title compound was prepared from the compound of Example 120 using the process described in Example 121.
$[\alpha]_D$=+304.09° (c=1, CHCl$_3$)

EXAMPLE 123

(−)-1-(4-Aminophenyl)-3-methylcarbamoyl-4-methyl-7,8-methylenedioxy-3,4-dihydro-5H-2,3-benzodiazepine A suspension of the compound prepared as described in Example 122 (2.42 g) and Raney nickel (W-2, 0.5 g) in methanol (50 ml) was treated with 98% hydrazine hydrate (1.1 ml). After stirring the reaction mixture for 1 hour at 25° C., the catalyst was removed by filtration, and the filtrate was evaporated in vacuo. The oily residue was treated with water (50ml). The resulting precipitate was filtered and dried to give 2.06 g of the crude solid. This material was dissolved in ethanol (10 ml) and concentrated to a small volume in vacuo. The residue was treated with benzene (26 ml) to induce crystallization. The crystalline product was collected by filtration, and dried at reduced pressure (36 hrs., 100° C., 80 torr), to give 1.98 g of the title compound as a light yellow powder. Melting point 133°–135° C.
$[\alpha]_D = -376.65°$ (c=1, CHCl$_3$)
Enantiomeric purity: >99%

EXAMPLE 124

(+)-1-(4-Aminophenyl)-3-methylcarbamoyl-4-methyl-7,8-methylenedioxy-3,4-dihydro-5H-2,3-benzodiazepine The title compound was prepared from the compound of Example 121 using the process described in Example 123. Melting point 133°–135° C.
$[\alpha]_D = +363.4°$ (c=1, CHCl$_3$)
Enantiomeric purity: >99%

EXAMPLE 125

(−)-1-(4-Nitrophenyl)-3-acetyl-4-methyl-7,8-methylenedioxy-3,4-dihydro-5H-2,3-benzodiazepine A mixture of the compound prepared as described in Example 119 (2.34 g) and acetic anhydride (11.7 ml) was stirred at room temperature. After 15 minutes, dissolution of the benzodiazepine was complete. After 2 hours, the reaction mixture was cooled in an ice-water bath and treated with water (60 ml). After stirring overnight, the crystalline product was collected, washed with water (4×5 ml), and dried to give 2.5 g of the title compound as pale yellow crystals. Melting point 173°–177° C.
$[\alpha]_D = -54.9°$ (c=1, CHCl$_3$)

EXAMPLE 126

(+)-1-(4-Nitrophenyl)-3-acetyl-4-methyl-7,8-methylenedioxy-3,4-dihydro-5H-2,3-benzodiazepine The title compound was prepared from the compound of Example 120 using the process described in Example 125. Melting point 173°–177° C.
$[\alpha]_D = +49.6°$ (c=1, CHCl$_3$)

EXAMPLE 127

(+)-1-(4-Aminophenyl)-3-acetyl-4-methyl-7,8-methylenedioxy-3,4-dihydro-5H-2,3-benzodiazepine A suspension of the compound prepared as described in Example 125 (2.6 g) and Raney nickel (W-2, 0.5 g) in methanol (52 ml) was treated with 98% hydrazine hydrate (1.2 ml). After stirring the reaction mixture for 1 hour at room temperature, the catalyst was removed by filtration, and the filtrate evaporated in vacuo. The oil residue was treated with water (50 ml). The resulting percipitate was filtered and dried to give 2.17 g of the crude solid. This material was recrstallized from ethyl acetate (39 ml), the crystalline product collected and dried (36 hrs, 120°–130° C., 80 torr) to give 1.8 g of the title compound. Melting 169°–171.5° C.
$[\alpha]_D = +313.41°$ (c=1, MeOH)
Enantiomeric purity: >99%

EXAMPLE 128

(−)-1-(4-Aminophenyl)-3-acetyl-4-methyl-7,8-methylenedioxy-3,4-dihydro-5H-2,3-benzodiazepine The title compound was prepared from the compound of Example 126 using the process described in Example 128. Melting point 169°–172° C.
$[\alpha]_D = -321.34°$ (c=1, MeOH)
Enantiomeric purity: >99%

We claim:
1. An N-Acyl-2,3-benzodiazepine derivative of the formula (I)

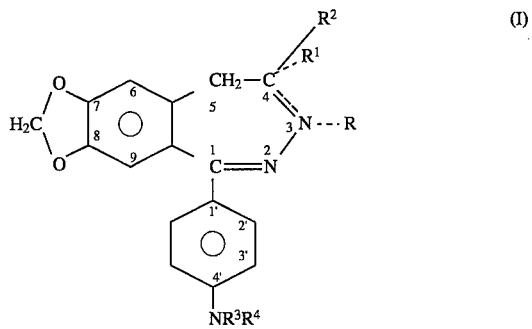

wherein
R is a $C_{1-6}$alkanoyl group optionally substituted by a methoxy, cyano, carboxyl, amino, $C_{1-4}$alkylamino, di($C_{1-4}$alkyl)amino, pyrrolidino, phthalimido or phenyl group, or by one or more halogen(s); or R is a benzoyl, cyclopropanecarbonyl, $C_{1-5}$alkylcarbamoyl or phenylcarbamoyl group; or R is absent when a double bond exists between the N(3) and C(4) atoms;
$R^1$ is hydrogen, or $R^1$ is absent when a double bond exists between the N(3) and C(4) atoms;
$R^2$ is a $C_{1-3}$alkyl group; or
$R^1$ and $R^2$ together form a methylene group;
$R^3$ is hydrogen or a $C_{1-4}$alkanoyl group;
$R^4$ is hydrogen; a $C_{1-6}$alkanoyl group optionally substituted by a methoxy, cyano, carboxyl, amino, $C_{1-4}$alkylamino, di($C_{1-4}$alkyl)amino, pyrrolidino, phthalimido or phenyl group or by one or more halogen(s); as well as a benzoyl, palmitoyl, cyclopropanecarbonyl, $C_{1-5}$alkylcarbamoyl or phenylcarbamoyl group;
with the proviso that no double bond exists between the N(3) and C(4) atoms when both $R^3$ and $R^4$ stand for hydrogen; and stereoisomers and acid-addition salts of said compound.

2. A compound selected from the group consisting of
[1-(4-aminophenyl)-3-acetyl-4-methyl-7,8-methylenedioxy-3,4 -dihydro-5H-2,3-benzodiazepine,]
1-(4-aminophenyl)-3-propionyl-4-methyl-7,8-methylenedioxy-3,4 -dihydro-5H-2,3-benzodiazepine,
1-(4-acetylaminophenyl)-3-acetyl-4-methyl-7,8-methylenedioxy-3,4 -dihydro-5H-2,3-benzodiazepine,
1-(4-propionylaminophenyl)-3-propionyl-4-methyl-7,8-methylenedioxy- 3,4-dihydro-5H-2,3-benzodiazepine,
1-(4-propionylaminophenyl)-3-acetyl-4-methyl-7,8-methylenedioxy- 3,4-dihydro-5H-2,3-benzodiazepine,
1-(4-acetylaminophenyl)-3-propionyl-4-methyl-7,8-methylenedioxy- 3,4-dihydro-5H-2,3-benzodiazepine,
1-(4-propionylaminophenyl)-3-formyl-4-methyl-7,8-methylenedioxy- 3,4-dihydro-5H-2,3-benzodiazepine,
1-(4-trifluoroacetylaminophenyl)-3-acetyl-4-methyl-7,8 -methylenedioxy-3,4-dihydro-5H-2,3-benzodiazepine,
1-(4-glycylaminophenyl)-3-acetyl-4-methyl-7,8-methylenedioxy-3,4 -dihydro-5H-2,3-benzodiazepine hydrochloride, $N^1$-[4-(3-acetyl-4-methyl-7,8-methylenedioxy-3,4-dihydro-5H-2,3 -benzodiazepine-1-yl)-phenyl]-$N^3$-methylurea, 1-[4-(N,N-dimethylglycylamino)phenyl]-3-acetyl-4-methyl-7,8 -methylenedioxy-3,4-dihydro-5H-2,3-benzodiazepine, 1-[4-(N,N-diethylglycylamino)phenyl]-3-acetyl-4-methyl-7,8-methylenedioxy-3,4-dihydro-5H-2,3-benzodiazepine, 1-[4-(1-pyrrolidinoacetylamino)phenyl]-3-acetyl-4-methyl-7,8 -methylenedioxy-3,4-dihydro-5H-2,3-benzodiazepine and hydrogen fumarate thereof, and 1-(4-glycylaminophenyl)-3-methylcarbamoyl-4-methyl-7,8 -methylenedioxy-3,4-dihydro-5H-2,3-benzodiazepine.

3. The N-acyl-2,3-benzodiazepine derivative of claim 1 which is 1-(4-aminophenyl)-3-acetyl-4-methyl-7,8-methylenedioxy-3,4 -dihydro-5H-2,3-benzodiazepine or its stereoisomer.

4. The N-acyl-2,3-benzodiazepine derivative of claim 3 which is (−)-1-(4-aminophenyl)-3-acetyl-4-methyl-7,8-methylenedioxy-3,4 -dihydro-5H-2,3-benzodiazepine.

5. The N-acyl-2,3-benzodiazepine derivative of claim 1 which is 1-(4-aminophenyl)-3-methylcarbamoyl-4-methyl-7,8-methylenedioxy- 3,4-dihydro-5H-2,3-benzodiazepine or its stereoisomer.

6. The N-acyl-2,3-benzodiazepine derivative of claim 5 which is (−)-1-(4-aminophenyl)-3-methylcarbamoyl-4-methyl-7,8 -methylenedioxy-3,4-dihydro-5H-2,3-benzodiazepine.

* * * * *

UNITED STATES PATENT AND TRADEMARK OFFICE
CERTIFICATE OF CORRECTION

PATENT NO. : 5,536,832
DATED : July 16, 1996
INVENTOR(S) : andrasi, et. al.

It is certified that error appears in the above-indentified patent and that said Letters Patent is hereby corrected as shown below:

Column 34, line 6, replace "Example 128" with --Example 127--.

Column 34, claim 2, lines 49-50, delete "[1-(4-aminophenyl)-3-acetyl-4-methyl-7,8-methylene-dioxy-3,4-dihydro-5H-2,3-benzodiazepine,]".

Signed and Sealed this

Twenty-sixth Day of November 1996

Attest:

BRUCE LEHMAN

*Attesting Officer*     Commissioner of Patents and Trademarks